(12) United States Patent
Diwu et al.

(10) Patent No.: US 8,431,416 B2
(45) Date of Patent: Apr. 30, 2013

(54) REACTIVE HETEROCYCLE-SUBSTITUTED 7-HYDROXYCOUMARINS AND THEIR CONJUGATES

(75) Inventors: Zhenjun Diwu, Sunnyvale, CA (US); Timothy Dubrovsky, Davis, CA (US); Barnaby Abrams, San Carlos, CA (US); Jinfang Liao, Foster City, CA (US); Qinglin Meng, Sunnyvale, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 184 days.

(21) Appl. No.: 12/726,267

(22) Filed: Mar. 17, 2010

(65) Prior Publication Data

US 2010/0255504 A1 Oct. 7, 2010

Related U.S. Application Data

(60) Provisional application No. 61/165,862, filed on Apr. 1, 2009.

(51) Int. Cl.
*G01N 33/533* (2006.01)
*C07K 1/13* (2006.01)
*C07K 16/00* (2006.01)

(52) U.S. Cl.
USPC .......... 436/546; 436/56; 530/391.3; 530/404; 530/405

(58) Field of Classification Search ................ None
See application file for complete search history.

(56) References Cited

U.S. PATENT DOCUMENTS

| | | | |
|---|---|---|---|
| 3,556,959 A | | 1/1971 | Passal |
| 4,235,781 A | | 11/1980 | Kaufman |
| 4,259,233 A | | 3/1981 | Carrico et al. |
| 4,296,039 A | | 10/1981 | della Valle |
| 4,452,811 A | | 6/1984 | della Valle |
| 5,696,157 A | * | 12/1997 | Wang et al. ............ 514/457 |
| 5,830,912 A | * | 11/1998 | Gee et al. ............... 514/457 |
| 6,372,895 B1 | * | 4/2002 | Bentsen et al. ......... 536/4.1 |
| 7,067,324 B2 | | 6/2006 | Knapp et al. |
| 7,173,130 B2 | | 2/2007 | Tsien et al. |
| 7,304,168 B2 | | 12/2007 | Li et al. |
| 2008/0071074 A1 | | 3/2008 | Skrzypczynski et al. |
| 2010/0029017 A1 | | 2/2010 | Diwu et al. |

FOREIGN PATENT DOCUMENTS

DE 3044128 11/1980

OTHER PUBLICATIONS

Kuziv et al. Synthesis of carboxyalkyl derivatives of 3-furylcoumarins for the fluorescent labeling of biomolecules. Ukrainica Bioorganica Acta 2009, vol. 2, pp. 47-54.*
Kentaro Azuma et al., "A study of the relationship between the chemical structures...," Photochem. Photobiol. Sci., vol. 2: 443-449 (2003).
Otto S. Wolfbeis et al. "The Unusually Strong Effect of a 4-Cyano Group upon Electronic Spectra and ..," The Chemical Society of Japan, vol. 58: 731-743 (1985).
European Search Report for EP Patent Application No. 10158457.1, Jun. 9, 2010.

* cited by examiner

*Primary Examiner* — Shafiqul Haq
(74) *Attorney, Agent, or Firm* — Bzicevic, Field & Francis LLP; Bret E. Field; Glenn J. Foulds

(57) ABSTRACT

Chemically-reactive, water-soluble, heterocycle-substituted 7-hydroxycoumarin dyes, their bioconjugates and uses are described. The conjugates derived from reactive heterocycle-substituted 7-hydroxycoumarin dyes are used for analyzing biological compounds. These heterocycle-substituted 7-hydroxycoumarin dyes are particularly useful as fluorescent labels for biopolymer detection reagents, such as antibodies or nucleic acid probes. The dye-antibody conjugates of the invention are particularly useful for analyzing analytes using a flow cytometer equipped with a violet laser as an excitation source due to their strong absorption at 405 nm and high fluorescence quantum yield.

22 Claims, 7 Drawing Sheets

Method A. Base-Catalyzed Condensation

Method B. Acetic Anhydride-Based Condensation

Anti-CD3 Antibody-Compound 7 Conjugates

Anti-CD4 Antibody-Compound 7 Conjugates

Anti-CD45 Antibody-Compound 7 Conjugates

US 8,431,416 B2

REACTIVE HETEROCYCLE-SUBSTITUTED 7-HYDROXYCOUMARINS AND THEIR CONJUGATES

BACKGROUND OF THE INVENTION

1. Field of the Invention

The invention relates to fluorescent chemicals, including reactive dyes and dye-conjugates; and to their uses.

2. Description of Related Art

Analyte-specific fluorescent probes are useful reagents for the analysis of analytes in a sample. The analytes become labeled through specific binding to the probes, and the labeling facilitates detection of the analyte. Applications of fluorescent probes for the analysis of analytes in a sample include fluorescence immunoassays, including the identification and/or separation of subpopulations of cells in a mixture of cells by flow cytometry, fluorescence microscopy, and visualization of gel separated analytes by fluorescence staining. These techniques are described by Herzenberg et al., "CELLULAR IMMUNOLOGY" 3rd ed., Chapter 22; Blackwell Scientific Publications (1978); and by Goldman, "FLUORESCENCE ANTIBODY METHODS" Academic Press, New York, (1968); and by Taylor et al., APPLICATIONS OF FLUORESCENCE IN THE BIOMEDICAL SCIENCES, Alan Liss Inc., (1986), each of which is incorporated herein by reference.

When employing fluorescent dyes for the above purposes, there are many considerations affecting the choice of the fluorescent dye. One consideration is the absorption and emission characteristics of the fluorescent dye, since many ligands, receptors, and materials in the sample under test, e.g., blood, urine, cerebrospinal fluid, will fluoresce and interfere with an accurate determination of the fluorescence of the fluorescent label. This phenomenon is called autofluorescence or background fluorescence. A second consideration is the ability to conjugate the fluorescent dye to ligands, receptors, and other biological and non-biological materials, and the effect of such conjugation on the fluorescent dye. In many situations, conjugation to another molecule may result in a substantial change in the fluorescent characteristics of the fluorescent dye and, in some cases, substantially destroy or reduce the quantum efficiency of the fluorescent dye. It is also possible that conjugation with the fluorescent dye will inactivate the function of the molecule that is labeled. A third consideration is the quantum efficiency of the fluorescent dye, which preferably is high for sensitive detection. A fourth consideration is the light absorbing capability, or extinction coefficient, of the fluorescent dyes, which preferably is as large as possible. A further consideration is whether the fluorescent molecules will interact with each other when in close proximity, resulting in self-quenching. Another consideration is whether there is non-specific binding of the fluorescent dye to other compounds or container walls, either by themselves or in conjunction with the compound to which the fluorescent dye is conjugated.

The applicability and value of the methods indicated above are closely tied to the availability of suitable fluorescent compounds. In particular, there is a need for fluorescent substances that can be excited by the commercial viable laser sources such as the violet laser (405 nm), argon laser (488 nm) and He—Ne laser (633 nm). There are many fluorescent dyes developed for argon laser (488 nm excitation) and He—Ne laser (633 nm excitation). For example, fluorescein, which is well excited by 488 nm argon laser, is a useful emitter in the green region. However, there are few fluorescent dyes available for the 405 nm violet laser.

Certain coumarin dyes have demonstrated utilities for a variety of biological detection applications. See, for example, U.S. Pat. No. 6,207,404 to Miller et al.; U.S. Pat. No. 5,830,912 to Gee et al.; and U.S. Pat. No. 4,956,480 to Robinson. Compared to other fluorescent dyes such as fluoresceins, rhodamines and cyanines, many coumarin dyes have certain advantageous properties. The smaller size of the coumarin dyes minimizes the effect of the dye on the affinity and specificity of a dye-labeled antigen-specific reagent. In addition, the smaller coumarins have higher labeling efficiency than fluoresceins, rhodamines and cyanines. Nevertheless, many coumarin dyes are known to share certain disadvantages, such as severe quenching of the fluorescence of hydroxyl coumarin dyes conjugated to proteins due to their strong hydrophobicity and high pKa. The coumarin fluorescence quenching results from self-quenching (close distance between coumarin tags) and/or from the quenching by electron-rich amino acid residues (such as histidine, tryptophan and tyrosine etc). In addition, the typically weak absorption at 405 nm of coumarins severely limits their applications for analyzing cells using a violet excitation laser, such as used in some flow cytometers.

Chlorinated coumarins have been used to label small organic molecules (e.g., Zlokarnik et al., 1998, Science 279: 84 and U.S. Pat. No. 5,955,604). For labeling small organic molecules, neither self-quenching nor the quenching by the substrate is a severe problem because only a single coumarin molecule is present in each conjugate. In contrast, for labeling antibodies, both self-quenching and quenching by the substrate are a significant concern because it is desirable to conjugate multiple dye molecules to each antibody. It is generally considered that chlorination of coumarins or fluoresceins would result in inferior labeling of antibodies due to the so called "heavy atom effect" and increased hydrophobicity (U.S. Pat. No. 5,516,629 to Park et al.; U.S. Pat. No. 5,830,912 to Gee et al.; U.S. Pat. No. 6,472,205 to Tsien and Zlokarnik; Haugland, Handbook of Fluorescent Probes and Research Chemicals, Molecular Probes, $9^{th}$ ed., pp 7-74, 2002).

Copending U.S. patent application Ser. No. 12/220,939, filed Jul. 29, 2008, incorporated herein by reference, describes antibodies conjugated to a plurality of mono-chlorinated, 7-hydroxycoumarin dyes, and their use in biological assays. These mono-chlorinated hydroxycoumarin dyes unexpectedly exhibit decreased self-quenching when used as antibody labels with multiple dyes per antibody. These dye-labeled antibodies typically exhibit absorbance maxima close to 405 nm and exhibit maximum emission in the blue.

SUMMARY OF THE INVENTION

The present invention provides water-soluble, heterocycle-substituted 7-hydroxycoumarin dyes and derivatives of water-soluble, heterocycle-substituted 7-hydroxycoumarin dyes, including reactive dyes and dye-conjugates.

The water-soluble, heterocycle-substituted 7-hydroxycoumarin dyes of the present invention exhibit novel combinations of properties that make these fluorescent dyes particularly suited for use in biological assays, including for use as labels for biopolymers. We discovered that the heterocycle-substitution and addition of water-soluble groups of 7-hydroxycoumarins unexpectedly results in a new class of fluorescent coumarins useful in biological assays and for preparing biological conjugates that have strong absorption at 405 nm and are highly fluorescent. In addition, the halogenation of heterocycle-substituted 7-hydroxycoumarins significantly decrease pKa of the coumarin dyes so that the resulted comarin conjugates have their maximum fluorescence in the range of physiological pH. These heterocycle-substituted 7-hydroxycoumarin dyes are strongly fluorescent, and the enhanced fluorescence intensity of the heterocycle-substituted 7-hydroxycoumarin dye-conjugates of the invention results in greater assay sensitivity.

The heterocycle-substituted 7-hydroxycoumarin dyes of the invention typically exhibit absorbance maxima close to 405 nm, and dyes of the invention can be selected to match the principal emission lines of a violet laser, as present in, for example, many flow cytometers. A particular advantage of the reactive dyes and dye conjugates of the present invention is that this class of dyes typically exhibit maximum emission in the green (approximately 500-540 nm). To our knowledge, the present invention provides the first description of a class of small molecule fluorescent dyes that emit in the green and are useful for labeling biological molecules under typical biological assay reaction conditions.

In one aspect, the present invention provides chemically-reactive, water-soluble, heterocycle-substituted 7-hydroxycoumarin compounds useful as fluorescent dyes. The reactive water-soluble, heterocycle-substituted 7-hydroxyl coumarin dyes of the invention can react with a wide variety of organic or inorganic substances ("substrate") that contain or are modified to contain functional groups with suitable reactivity, resulting in conjugation of the dye to the substance. In one aspect of the invention, the reactive dyes of the invention are used to directly fluorescently stain or label a sample so that the sample can be detected, identified, or quantitated.

In another aspect, the present invention provides dye-conjugates that comprise one or more water-soluble, heterocycle-substituted 7-hydroxycoumarins of the invention conjugated to a substrate. In preferred embodiments, the dye-conjugates are used as fluorescent detection reagents to detect, identify, locate, or quantitate analytes in a sample.

In a preferred embodiment of the invention, the dye-conjugate substrate is a biopolymer, and the biopolymer is conjugated to a one or more or the water-soluble, heterocycle-substituted 7-hydroxycoumarins of the invention to obtain a fluorescent biopolymer. The fluorescent biopolymer dye-conjugates of the invention have utility as, or as part of, detection reagents, including analyte-specific detection reagents. Useful biopolymers include, for example, amino acid polymers, nucleic acid polymers, polysaccharides, carbohydrates, and lipids. In a preferred embodiment, the biopolymer component of the dye-biopolymer conjugate is an amino acid polymer, as broadly defined herein. In a preferred embodiment, the biopolymer is a monoclonal antibody.

In another aspect, the present invention provides kits containing the reactive dyes or dye-conjugates of the present invention. Kits of the present invention can contain additional components useful for carrying out the intended application, such as other reagents or buffers.

The reactive water-soluble, heterocycle-substituted 7-hydroxycoumarin dyes of the invention have the structure of Formula 1:

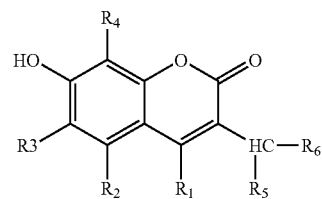

Formula 1 wherein
HC is a heterocycle;
$R_1$, $R_2$, $R_3$, $R_4$, $R_5$, and $R_6$ are independently H, halogen, alkyl, alkoxy, aryloxy, thiol, alkylthiol, arylthiol, azido, amino, hydroxy, sulfonyl, phosphonyl, boronic acid, L-RG, WSG, or alkyl or alkoxy that is itself substituted one or more times by halogen, amino, hydroxy, sulfonyl, phosphonyl, carbonyl, boronic acid, L-RG, or WSG;
RG is a chemically reactive group;
L is an optional linker;
WSG is a water-soluble group;
at least one of $R_1$, $R_2$, $R_3$, $R_4$, $R_5$, and $R_6$ contains L-RG; and
at least one of $R_1$, $R_2$, $R_3$, $R_4$, $R_5$, and $R_6$ is WSG.

Preferably, the heterocycle moiety, HC, is selected from the following:

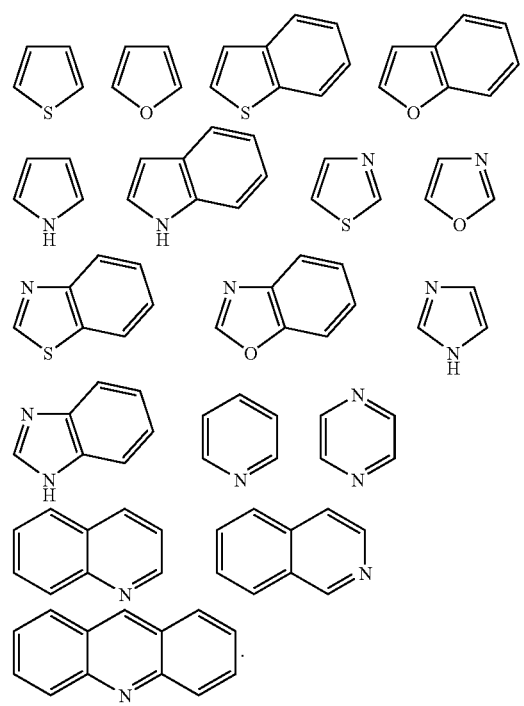

Preferably, the reactive group, RG, is an acrylamide, an amine, a carboxylic acid, an activated ester of a carboxylic acid, an acyl azide, an acyl nitrile, an aldehyde, an alkyl halide, an anhydride, an aryl halide, an azide, an aziridine, a boronate, a diazoalkane, a haloacetamide, a halotriazine, a hydrazine, a hydroxylamine, an imido ester, an isocyanate, an isothiocyanate, a maleimide, a reactive platinum complex, a sulfonyl halide or a psoralen derivative.

Preferably, the optional linker, L, is none, an alkyl, alkoxy, a thioalkyl, an amino acid, a sulfo amino acid, polyamine, a polyethyleneglycol, an aryl, or a heteroaryl.

Preferably, the water-soluble group, WSG, is a sulfonate, a thiosulfonate, a phosphonate, a boronate, an ammonium, a pyridium, a quinolium or an acridinium group.

In a preferred embodiment, the reactive water-soluble, heterocycle-substituted 7-hydroxycoumarin dyes of the present invention have the structure of Formula 2:

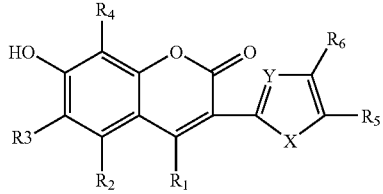

Formula 2 wherein
- X is O, S, NH or $NR_{10}$;
- Y is NH, $NR_{11}$, CH, or $CR_{12}$;
- $R_1, R_2, R_3, R_4, R_5, R_6, R_{10}, R_{11}$, and $R_{12}$, are independently H, halogen, alkyl, alkoxy, aryloxy, thiol, alkylthiol, arylthiol, azido, amino, hydroxy, sulfonyl, phosphonyl, boronic acid, L-RG, WSG, or alkyl or alkoxy that is itself optionally substituted one or more times by halogen, amino, hydroxy, sulfonyl, phosphonyl, carbonyl, boronic acid, L-RG, or WSG;
- RG is a chemical reactive group;
- L is an optional linker;
- WSG is a water-soluble group;
- at least one of $R_1, R_2, R_3, R_4, R_5, R_6, R_{10}, R_{11}$, and $R_{12}$ contains L-RG; and
- at least one of $R_1, R_2, R_3, R_4, R_5, R_6, R_{10}, R_{11}$, and $R_{12}$ is WSG.

In another preferred embodiment, the reactive water-soluble, heterocycle-substituted 7-hydroxycoumarin dyes have the structure of Formula 3:

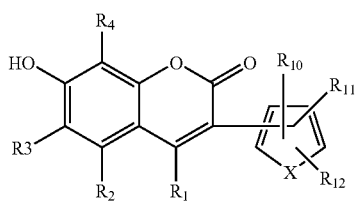

Formula 3 wherein
- X is O or S;
- $R_1, R_2, R_3, R_4, R_{10}, R_{11}$, and $R_{12}$ are independently H, halogen, alkyl, alkoxy, aryloxy, thiol, alkylthiol, arylthiol, azido, amino, hydroxy, sulfonyl, phosphonyl, boronic acid, L-RG, WSG, or alkyl or alkoxy that is itself optionally substituted one or more times by halogen, amino, hydroxy, sulfonyl, phosphonyl, carbonyl, boronic acid, L-RG, or WSG;
- RG is a chemical reactive group;
- L is an optional linker;
- WSG is a water-soluble group;
- at least one of $R_1, R_2, R_3, R_4, R_{10}, R_{11}$ and $R_{12}$ contains L-RG; and
- at least one of $R_1, R_2, R_3, R_4, R_{10}, R_{11}$ and $R_{12}$ is WSG.

In another preferred embodiment, the reactive water-soluble, heterocycle-substituted 7-hydroxycoumarin dyes of the invention have the structure of Formula 4:

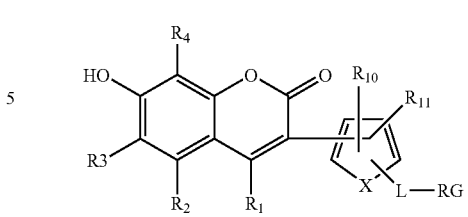

Formula 4 wherein
- X is O or S;
- $R_1, R_2, R_3, R_4, R_{10}$, and $R_{11}$ are independently H, halogen, alkyl, alkoxy, aryloxy, thiol, alkylthiol, arylthiol, azido, amino, hydroxy, sulfonyl, phosphonyl, boronic acid, L-RG, WSG, or alkyl or alkoxy that is itself optionally substituted one or more times by halogen, amino, hydroxy, sulfonyl, phosphonyl, carbonyl, boronic acid, L-RG, or WSG;
- RG is a chemical reactive group;
- L is an optional linker;
- WSG is a water-soluble group;
- at least one of $R_1, R_2, R_3, R_4, R_{10}$, and $R_{11}$ contains L-RG;
- at least one of $R_1, R_2, R_3, R_4, R_{10}$, and $R_{11}$ is WSG; and
- at least one of $R_{10}$ and $R_{11}$ contains a sulfonate.

In another preferred embodiment, the reactive water-soluble, heterocycle-substituted 7-hydroxycoumarin dyes of the invention have the structure of Formula 5:

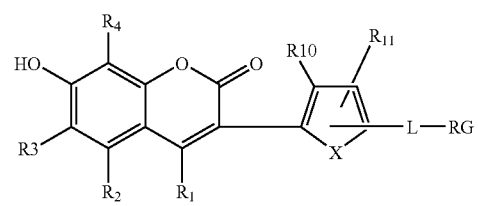

Formula 5 wherein
- X is O or S;
- $R_1, R_2, R_3, R_4, R_{10}$, and $R_{11}$ are independently hydrogen, chloro, fluoro, cyano, or sulfonate;
- RG is a chemical reactive group;
- L is an optional linker, and
- wherein at least one of $R_{10}$ and $R_{11}$ is a sulfonate.

In another preferred embodiment, the reactive water-soluble, heterocycle-substituted 7-hydroxycoumarin dyes of the invention have the structure of Formula 6:

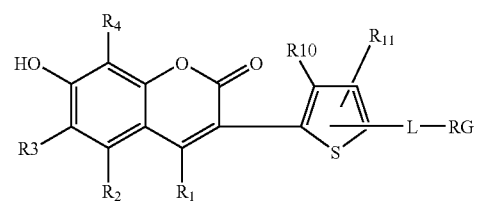

Formula 6 wherein
- $R_1, R_2, R_3, R_4, R_{10}$, and $R_{11}$ are independently hydrogen, chloro, fluoro, cyano, or sulfonate;
- RG is a chemical reactive group;

L is an optional linker that is none, alkyl, alkoxy, thioalkyl, an amino acid, a sulfo amino acid, polyamine, polyethyleneglycol, aryl, arylalky, or heteroaryl, and wherein at least one of $R_{10}$ and $R_{11}$ is a sulfonate.

In another preferred embodiment, the reactive water-soluble, heterocycle-substituted 7-hydroxycoumarin dyes of the invention have the structure of Formula 7:

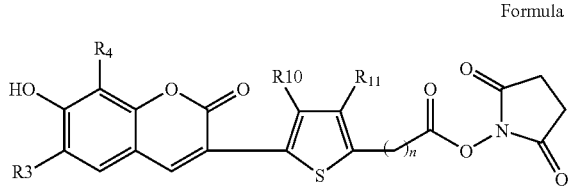

Formula 7 wherein
$R_3$, $R_4$, $R_{10}$, and $R_{11}$ are independently hydrogen, chloro, fluoro, cyano, or sulfonate;
n is an integer of 1-10; and wherein at least one of $R_{10}$ and $R_{11}$ is a sulfonate.

In another preferred embodiment, the reactive water-soluble, heterocycle-substituted 7-hydroxycoumarin dyes of the invention have the structure of Formula 8:

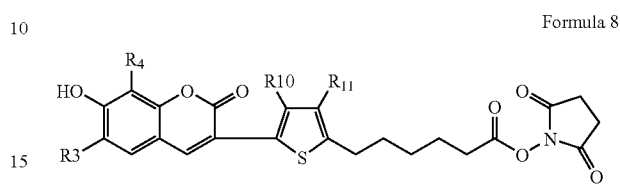

Formula 8 wherein
$R_3$ and $R_4$ are independently hydrogen, chloro, fluoro or sulfonate; and
at least one of $R_{10}$ and $R_{11}$ is a sulfonate.

Selected embodiments of the reactive dyes of the present invention are given in Table 1, below. The number of the reactive dyes in Table 1 corresponds to the numbering of the compounds described in the examples.

TABLE 1

Example Reactive Dyes of the Invention

| Dye | Structure |
|---|---|
| 6 | ![structure 6] |
| 7 | ![structure 7] |
| 8 | ![structure 8] |

TABLE 1-continued
Example Reactive Dyes of the Invention
| Dye | Structure |
|---|---|
| 9 | 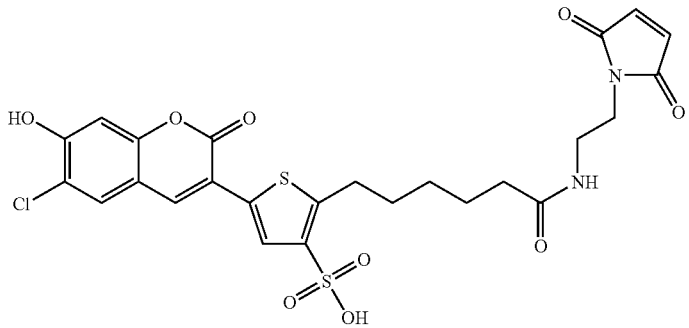 [SMILES: O=C(CCCCCc1sc(-c2cc3cc(Cl)c(O)cc3oc2=O)cc1S(=O)(=O)O)NCCN1C(=O)C=CC1=O] |
| 13A | 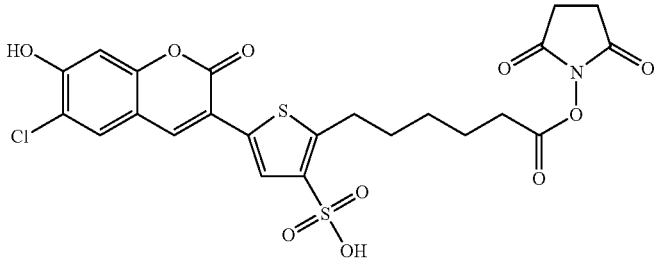 [SMILES: O=C(CCCCCc1sc(-c2cc3cc(Cl)c(O)cc3oc2=O)cc1S(=O)(=O)O)ON1C(=O)CCC1=O] |
| 14 | 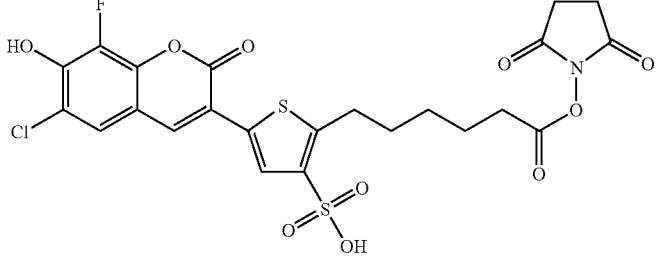 |
| 19 | 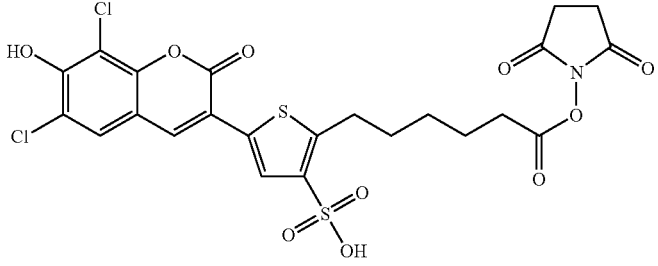 [SMILES: O=C(CCCCCc1sc(-c2cc3cc(Cl)c(O)c(F)c3oc2=O)cc1S(=O)(=O)O)ON1C(=O)CCC1=O] |

TABLE 1-continued
Example Reactive Dyes of the Invention
| Dye | Structure |
|---|---|
| 25 | 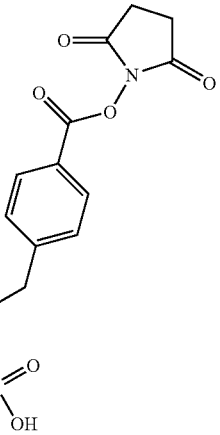 |
| 29 | 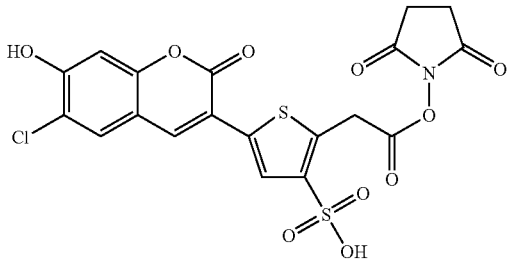 [SMILES: O=C(Cc1sc(-c2cc3cc(Cl)c(O)cc3oc2=O)cc1S(=O)(=O)O)ON1C(=O)CCC1=O] |
| 36 | 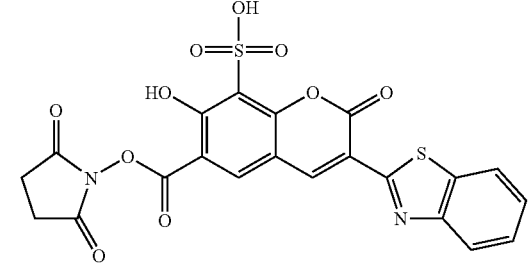 [SMILES: O=C(ON1C(=O)CCC1=O)c1cc2cc(-c3nc4ccccc4s3)c(=O)oc2c(S(=O)(=O)O)c1O] |
| 40 | 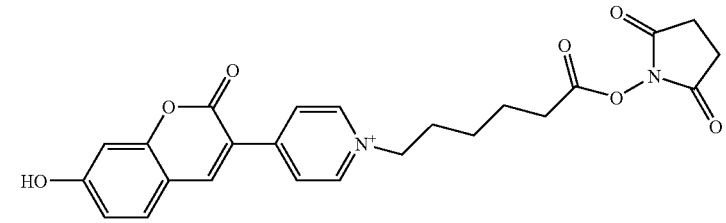 [SMILES: O=C(CCCCC[n+]1ccc(-c2cc3ccc(O)cc3oc2=O)cc1)ON1C(=O)CCC1=O] |
| 50 | 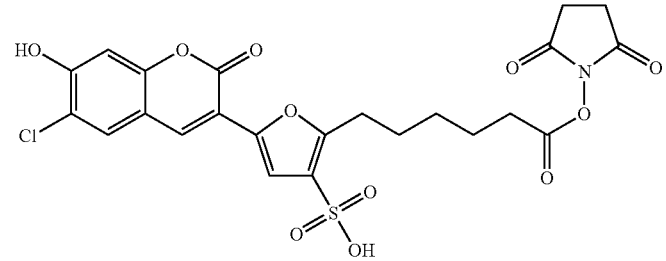 |

TABLE 1-continued

Example Reactive Dyes of the Invention

| Dye | Structure |
|-----|-----------|
| 56 | 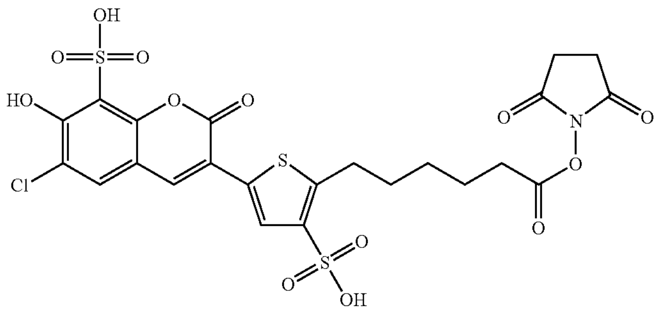 [SMILES: O=C(CCCCCc1sc(-c2cc3cc(Cl)c(O)c(S(=O)(=O)O)c3oc2=O)cc1S(=O)(=O)O)ON1C(=O)CCC1=O] |
| 60 | 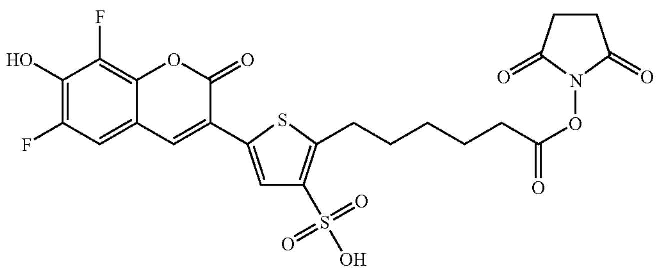 |
| 66 | 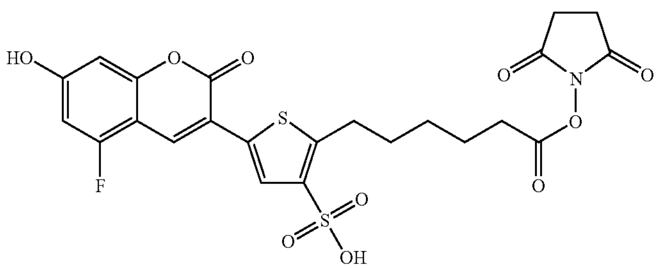 [SMILES: O=C(CCCCCc1sc(-c2cc3c(F)cc(O)cc3oc2=O)cc1S(=O)(=O)O)ON1C(=O)CCC1=O] |
| 70 | 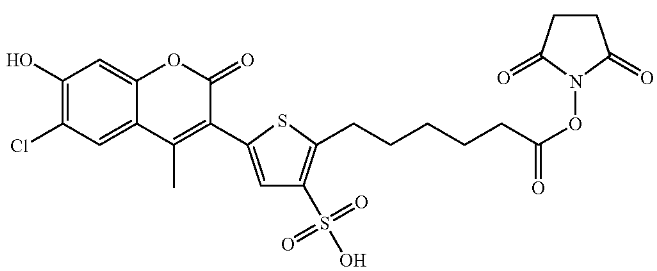 [SMILES: Cc1c(-c2cc(S(=O)(=O)O)c(CCCCCC(=O)ON3C(=O)CCC3=O)s2)c(=O)oc2cc(O)c(Cl)cc12] |
| 72 | 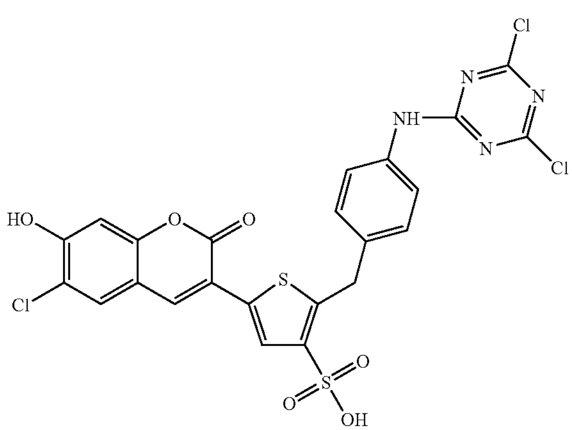 [SMILES: O=c1oc2cc(O)c(Cl)cc2cc1-c1cc(S(=O)(=O)O)c(Cc2ccc(Nc3nc(Cl)nc(Cl)n3)cc2)s1] |

TABLE 1-continued

Example Reactive Dyes of the Invention

| Dye | Structure |
|-----|-----------|
| 75  | 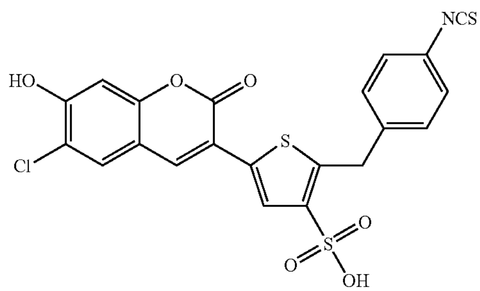 |
| 77  | 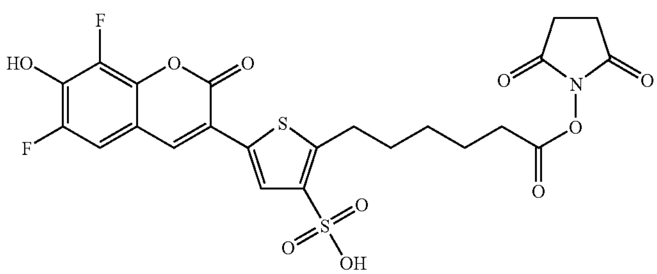 |
| 100 | 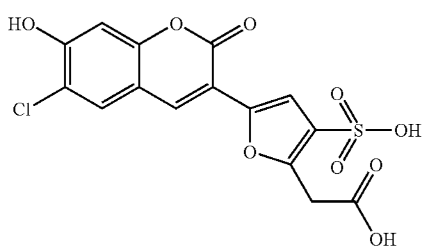 [SMILES: O=C(O)Cc1oc(-c2cc3cc(Cl)c(O)cc3oc2=O)cc1S(=O)(=O)O] |
| 101 | 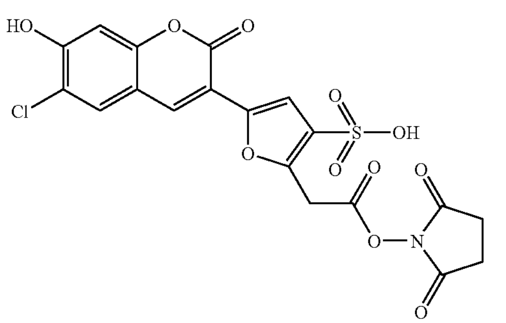 [SMILES: O=C(Cc1oc(-c2cc3cc(Cl)c(O)cc3oc2=O)cc1S(=O)(=O)O)ON1C(=O)CCC1=O] |
| 102 | 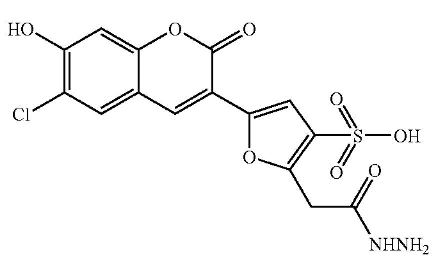 [SMILES: NNC(=O)Cc1oc(-c2cc3cc(Cl)c(O)cc3oc2=O)cc1S(=O)(=O)O] |

TABLE 1-continued

Example Reactive Dyes of the Invention

| Dye | Structure |
|---|---|
| 103 | 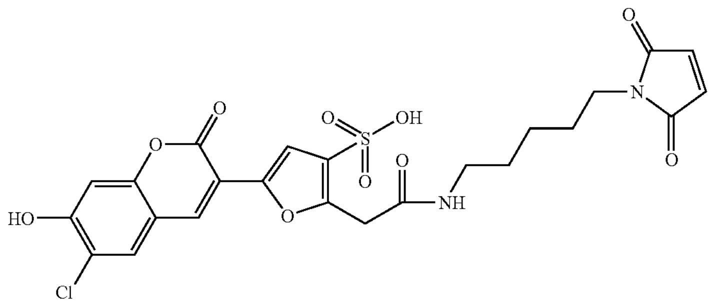 [SMILES: O=C(Cc1oc(-c2cc3cc(Cl)c(O)cc3oc2=O)cc1S(=O)(=O)O)NCCCCCN1C(=O)C=CC1=O] |
| 104 | 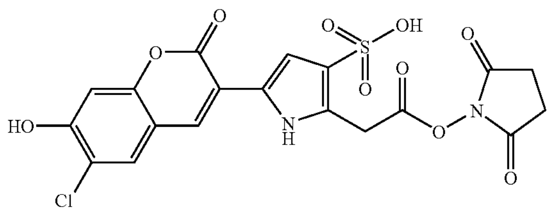 [SMILES: O=C(Cc1[nH]c(-c2cc3cc(Cl)c(O)cc3oc2=O)cc1S(=O)(=O)O)ON1C(=O)CCC1=O] |
| 105 | 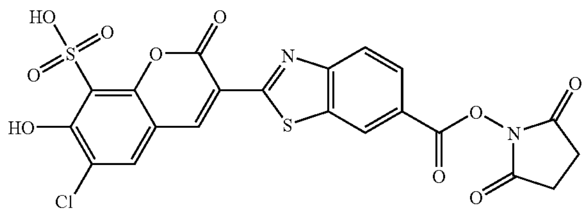 [SMILES: O=C(ON1C(=O)CCC1=O)c1ccc2nc(-c3cc4cc(Cl)c(O)c(S(=O)(=O)O)c4oc3=O)oc2c1] |
| 106 | 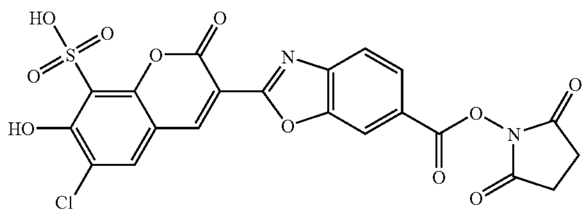 |
| 107 | 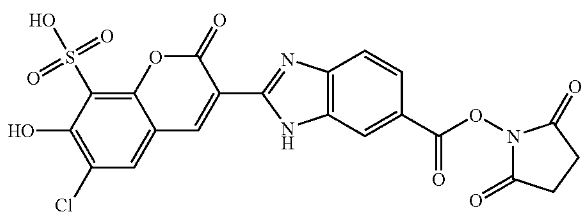 [SMILES: O=C(ON1C(=O)CCC1=O)c1ccc2nc(-c3cc4cc(Cl)c(O)c(S(=O)(=O)O)c4oc3=O)[nH]c2c1] |
| 108 | 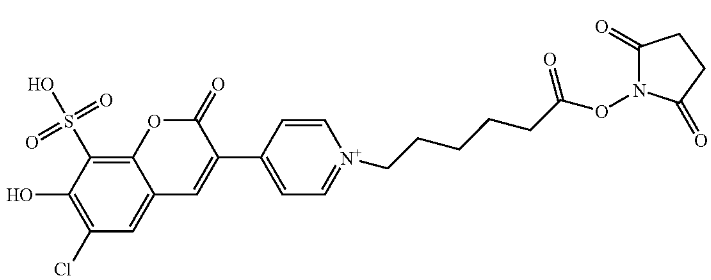 [SMILES: O=C(CCCCC[n+]1ccc(-c2cc3cc(Cl)c(O)c(S(=O)(=O)O)c3oc2=O)cc1)ON1C(=O)CCC1=O] |

TABLE 1-continued

Example Reactive Dyes of the Invention

| Dye | Structure |
| --- | --- |
| 109 | 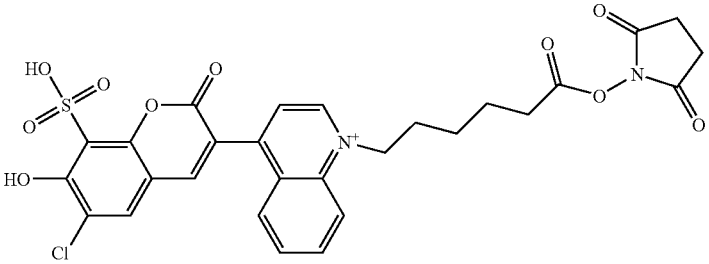 [SMILES: O=C(CCCCC[n+]1ccc(-c2cc3cc(Cl)c(O)c(S(=O)(=O)O)c3oc2=O)c2ccccc21)ON1C(=O)CCC1=O] |
| 110 | 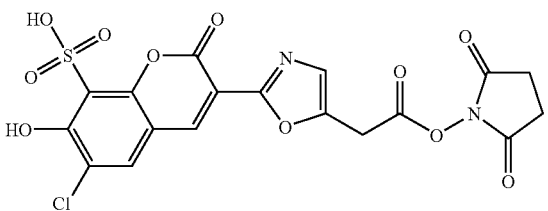 [SMILES: O=C(Cc1cnc(-c2cc3cc(Cl)c(O)c(S(=O)(=O)O)c3oc2=O)s1)ON1C(=O)CCC1=O] |
| 111 | 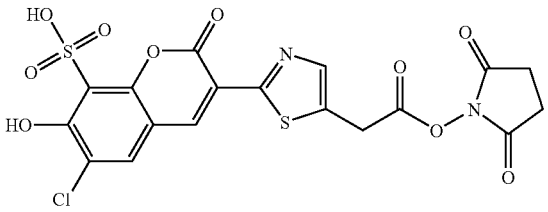 |

The dye-conjugates of the invention comprise a substrate to which one or more dyes of the invention are conjugated. Typically, the dye-conjugates are produced by a reaction between a reactive dye of the invention and a substrate that contains or has been modified to contain functional groups with suitable reactivity, resulting in chemical attachment of the dye to the substrate. As a result of the conjugation reaction between the reactive dye and the functional groups on the substrate, one or more atoms of the dye reactive group typically are incorporated into a new linkage attaching the dye to the substrate.

In general, the dye-conjugates of the invention have the structure of Formula 9:

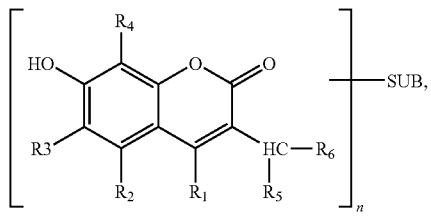

Formula 9 wherein
HC is a heterocycle;
$R_1$, $R_2$, $R_3$, $R_4$, $R_5$, and $R_6$ are independently H, halogen, alkyl, alkoxy, aryloxy, thiol, alkylthiol, arylthiol, azido, amino, hydroxy, sulfonyl, phosphonyl, boronic acid, WSG, or alkyl or alkoxy that is itself substituted one or more times by halogen, amino, hydroxy, sulfonyl, phosphonyl, carbonyl, boronic acid, or WSG;

WSG is a water-soluble group;
n is an integer of 1-35;
SUB is a substrate;
at least one of $R_1$, $R_2$, $R_3$, $R_4$, $R_5$, and $R_6$ is covalently bound to SUB through an optional linker L; and
at least one of $R_1$, $R_2$, $R_3$, $R_4$, $R_5$, and $R_6$ is WSG.

In a preferred embodiment, the dye-conjugate of the present invention has the structure of Formula 10:

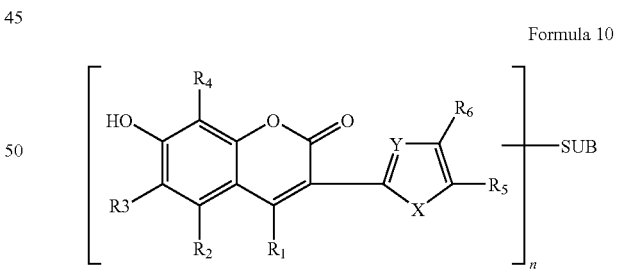

Formula 10 wherein
X is O, S, NH or $NR_{10}$;
Y is NH, $NR_{11}$, CH, or $CR_{12}$;
$R_1$, $R_2$, $R_3$, $R_4$, $R_5$, $R_6$, $R_{10}$, $R_{11}$, and $R_{12}$, are independently H, halogen, alkyl, alkoxy, aryloxy, thiol, alkylthiol, arylthiol, azido, amino, hydroxy, sulfonyl, phosphonyl, boronic acid, WSG, or alkyl or alkoxy that is itself optionally substituted one or more times by halogen, amino, hydroxy, sulfonyl, phosphonyl, carbonyl, boronic acid, or WSG;
WSG is a water-soluble group;

n is an integer of 1-35;

SUB is a substrate;

at least one of $R_1$, $R_2$, $R_3$, $R_4$, $R_5$, $R_6$, $R_{10}$, $R_{11}$, and $R_{12}$ is covalently bound to SUB through an optional linker L; and at least one of $R_1$, $R_2$, $R_3$, $R_4$, $R_5$, $R_6$, $R_{10}$, $R_{11}$, and $R_{12}$ is WSG.

In another preferred embodiment, the dye-conjugate of the present invention has the structure of Formula 11:

Formula 11

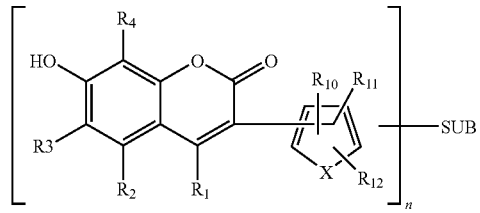

wherein

X is O or S;

$R_1$, $R_2$, $R_3$, $R_4$, $R_{10}$, $R_{11}$, and $R_{12}$ are independently H, halogen, alkyl, alkoxy, aryloxy, thiol, alkylthiol, arylthiol, azido, amino, hydroxy, sulfonyl, phosphonyl, boronic acid, WSG, or alkyl or alkoxy that is itself optionally substituted one or more times by halogen, amino, hydroxy, sulfonyl, phosphonyl, carbonyl, boronic acid, or WSG;

WSG is a water-soluble group;

n is an integer of 1-35;

SUB is a substrate;

at least one of $R_1$, $R_2$, $R_3$, $R_4$, $R_{10}$, $R_{11}$, and $R_{12}$ is covalently bound to SUB through an optional linker L; and at least one of $R_1$, $R_2$, $R_3$, $R_4$, $R_{10}$, $R_{11}$, and $R_{12}$ is WSG.

In another preferred embodiment, the dye-conjugate of the present invention has the structure of Formula 12:

Formula 12

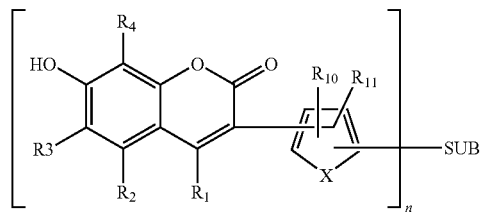

wherein

X is O or S;

$R_1$, $R_2$, $R_3$, $R_4$, $R_{10}$, and $R_{11}$ are independently H, halogen, alkyl, alkoxy, aryloxy, thiol, alkylthiol, arylthiol, azido, amino, hydroxy, sulfonyl, phosphonyl, boronic acid, WSG, or alkyl or alkoxy that is itself optionally substituted one or more times by halogen, amino, hydroxy, sulfonyl, phosphonyl, carbonyl, boronic acid, or WSG;

WSG is a water-soluble group;

n is an integer of 1-35;

SUB is a substrate;

at least one of $R_1$, $R_2$, $R_3$, $R_4$, $R_{10}$, and $R_{11}$ is covalently bound to S through an optional linker L;

at least one of $R_1$, $R_2$, $R_3$, $R_4$, $R_{10}$, and $R_{11}$ is WSG; and at least one of $R_{10}$ and $R_{11}$ contains a sulfonate.

In another preferred embodiment, the dye-conjugate of the present invention has the structure of Formula 13:

Formula 13

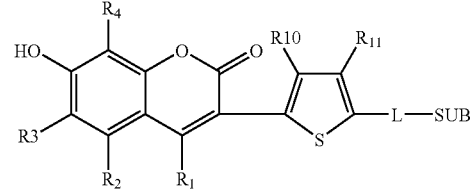

wherein

X is O or S;

$R_1$, $R_2$, $R_3$, $R_4$, $R_{10}$, and $R_{11}$ are independently hydrogen, chloro, fluoro, cyano, or sulfonate;

L is an optional linker;

SUB is a substrate; and wherein at least one of $R_{10}$ and $R_{11}$ is a sulfonate.

Preferred embodiments of the heterocycle moieties, linkers, and water-soluble groups are as described for the reactive dyes, above.

DETAILED DESCRIPTION OF THE INVENTION

Figure 1A:
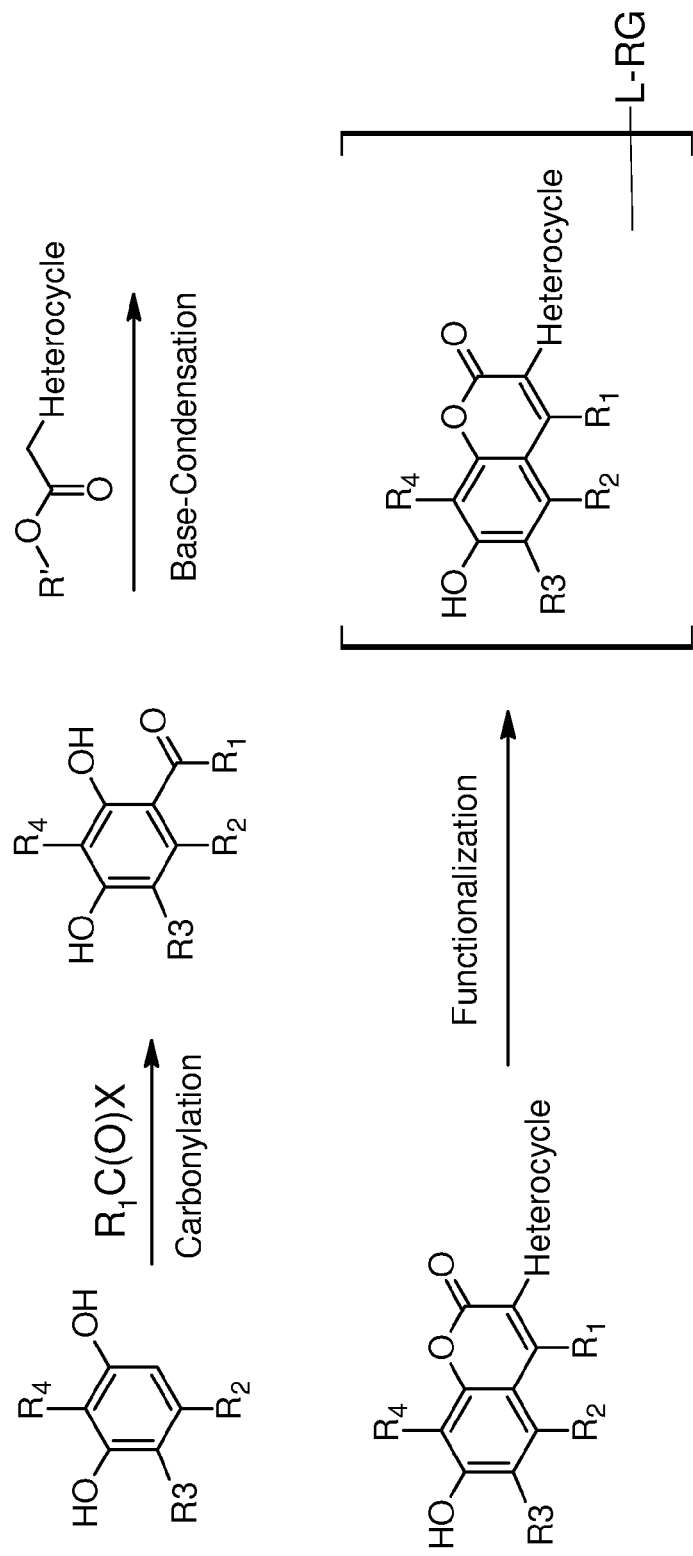
FIG. 1 shows a schematic of the synthesis of reactive coumarins by base-catalyzed condensation (Method A) or by acetic anhydride-based condensation (Method B) of 4-carbonylresorcinols with heterocycle acetate compounds.

In order that the invention herein described may be fully understood, a number of terms are explicitly defined, below. Terms not explicitly defined are intended to have their usual meaning in the fields of chemistry and biology. All references cited herein, both supra and infra, are incorporated herein by reference.

The term "7-hydroxycoumarin" or "7-hydroxycoumarin derivative", as used herein, by itself or as part of another group, means any compound or substituent that contains one or more of the following fused ring structures or a derivative thereof:

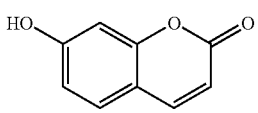

7-Hydroxycoumarin

It is to be understood that the coumarin dyes of the invention have been drawn in one or another particular electronic resonance structure. Every aspect of the instant invention applies equally to dyes that are formally drawn with other permitted resonance structures, as the electronic charge on the subject dyes are delocalized throughout the dye itself.

The term "heteroatom", as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "heterocycle" or "heteroaryl", as used herein, by itself or as part of another group, refers to groups having 5 to 14 ring atoms and containing carbon atoms and 1, 2, 3, or 4 oxygen, nitrogen or sulfur heteroatoms. Examples of heterocycle groups include thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups). Heterocycle groups have been described extensively in the literature (see, for example, Katritzky, Alan R., Charles W. Rees, and Colin J. Drayton. 1984. *Comprehensive heterocyclic chemistry: the structure, reactions, synthesis, and uses of heterocyclic compounds*. Volume 8, Part 6. Indexes. Oxford [Oxfordshire]: Pergamon Press., incorporated herein by reference).

Any aryl or heteroaryl ring system may be unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The term "substituted", as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxyalkyl)amino, alkoxycarbonyl, alkynylcarbonyl, alkylsulfonyl, alkenylsulfonyl, alkynylsulfonyl, arylsulfonyl, alkylsulfonyl, alkylsulfinyl, alkylsulfonamido, arylsulfonamido, alkylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

As used herein, a "reactive group", denoted "RG", refers to a moiety on a compound that is capable of chemically reacting with a functional group on a different compound to form a covalent linkage.

As used herein, a "linker", denoted "L", between two moieties is referred to as "optional" if the two moieties can be bound either directly to each other or through the linker as an intermediate. This language is used to simplify the description of alternative structures that differ only by the presence or absence of the linker. In the present invention, for example, the coumarin dye molecules can be conjugated either directly to the biopolymer or, alternatively, indirectly to the biopolymer through linker, L. For economy of notation, both alternatives are described herein by a single structure having an optional linker. An embodiment of a structure having an optional linker, L, in which the linker is not present can be described as the structure in which L is "none".

The term "water-soluble group" or "WSG", as used herein, refers to any substituent that enhances the water-solubility of a compound to which it is bound. Preferably, the water-soluble group, WSG, is a sulfonate, a thiosulfonate, a phosphonate, a boronate, an ammonium, a pyridium, a quinolium, an acridinium, or a polyhydroxy (e.g., a sugar such as glucose) group.

The term "sulfonate", by itself or as part of another group, refers to any compound or substituent that contains one or more moieties having the following structure:

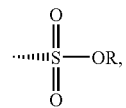

where R is hydrogen or other counter ions, such as a metal ion or ammonium ion.

As used herein, the term "dye-conjugate" refers to a conjugate between a dye and a "substrate" or "substance".

The term "analyte" is used herein broadly to refer to any substance to be analyzed, detected, measured, or labeled. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof. By convention, where cells of a given cell type are to be detected, both the cellular component molecules or the cell itself can be described as an analyte.

The term "analyte-specific reagent" or "target-specific reagent" is used herein broadly to refer to any reagent that preferentially binds to an analyte or target of interest, relative to other analytes potentially present in a sample. A target (analyte) and target-specific (analyte-specific) reagent are members of a binding pair, and either member of the pair can be used as the target-specific reagent in order to selectively bind to the other member of the pair. Examples of target and target-specific reagent pairs include, but are not limited to, are provided in the Table 2, below. Preferred target-specific reagents are antibodies that include an antigen binding site that specifically binds (immunoreacts with) an antigen.

TABLE 2

Representative specific binding pairs

| Antigen | Antibody |
|---|---|
| Biotin | Avidin, streptavidin, or anti-biotin Antibody |
| IgG (an immunoglobulin) | protein A or protein G |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| Nucleic acid | Nucleic acid |
| Hormone | Hormone receptor |
| Psoralen | Nucleic acid |
| Target molecule | RNA or DNA aptamer |

As used herein, a "detection reagent" refers to any compound that is used to facilitate optical detection of an analyte. A detection reagent typically comprises an analyte-specific reagent conjugated to a fluorescent label, and includes both dye-conjugates in which the substrate component, typically a biopolymer, is, itself, an analyte-specific reagent, and analyte specific reagents bound to a dye-conjugate that functions as the fluorescent label.

As used herein, the term "biopolymer" is used generically to refer to amino acid polymers, nucleic acid polymers, carbohydrates, polysaccharides, and lipids, each as broadly defined herein.

As used herein, the term "amino acid polymer" is used generically to refer to any polymer of amino acids, including peptides, polypeptides, and proteins, including proteins that have been subject to co-translational or post-translational modification, such as glycoproteins. The amino acid polymer may comprise both standard (i.e., one of the 20 amino acids encoded by the standard genetic code, also referred to as proteinogenic) and nonstandard amino acids, may be derivatized, protected, or substituted, such as, for example, by phosphates, carbohydrates, or $C_1$ to $C_{25}$ carboxylic acids. The terms "peptide", "polypeptide", and "protein" are used herein interchangeably without a distinction as to the length of the polymer, although short polymers of amino acids are typically referred to as peptides or polypeptides and longer polymers of amino acids, particularly those that are naturally occurring and/or have a biological function, are referred to as proteins.

As used herein, the term "antibody" includes all products, derived or derivable from antibodies or from antibody genes, that are useful as target-specific binding reagents. "Antibody" thus includes, inter alia, natural antibodies, antibody fragments, antibody derivatives, and genetically-engineered antibodies, antibody fragments, and antibody derivatives.

As used herein, the terms "nucleic acid polymer", "nucleic acid", and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Nucleic acid polymers is intended to include peptide nucleic acids, such as N-(2-aminoethyl)glycine units (see Nielsen et al., U.S. Pat. No. 5,539,082, incorporated herein by reference).

Reactive Dyes

The reactive water-soluble, heterocycle-substituted 7-hydroxyl coumarins of the present invention have the general structure shown in any of Formulae 1-8. Particular examples are shown in Table 1 and described in the examples.

The reactive water-soluble, heterocycle-substituted 7-hydroxyl coumarin dyes contain at one reactive group, RG, covalently attached to the dye by an optional linker L. In certain embodiments, the covalent linkage attaching the dye to RG contains multiple intervening atoms that serve as a spacer.

The reactive water-soluble, heterocycle-substituted 7-hydroxyl coumarins dyes of the invention can react with a wide variety of organic or inorganic substances that contain or are modified to contain functional groups with suitable reactivity, resulting in chemical attachment to the dye to the substance. Typically, the conjugation reaction between the reactive dye and the functional groups on the substance results in one or more atoms of the reactive group RG to be incorporated into a new linkage attaching the dye to the substance.

Typically, a reactive group is an electrophile or nucleophile that can form a covalent linkage through exposure to a corresponding functional group that is a nucleophile or electrophile, respectively. Selected examples of reactive pairs of electrophilic and nucleophilic groups, along with the covalent linkage resulting from their reaction, are shown in Table 3, below.

TABLE 3

Reactive Electrophilic and Nucleophilic groups, and the Resulting Conjugates

| Electrophilic Group | Nucleophilic Group | Resulting Conjugate |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic adds | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |

TABLE 3-continued

Reactive Electrophilic and Nucleophilic groups, and the Resulting Conjugates

| Electrophilic Group | Nucleophilic Group | Resulting Conjugate |
|---|---|---|
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula -COW, where W is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride -OCOAlk or —OCN(Alk$_1$)NH(Alk$_2$), where Alk$_1$ and Alk$_2$, which may be the same or different, are C$_1$-C$_{20}$ alkyl, C$_1$-C$_{20}$ perfluoroalkyl, or C$_1$-C$_{20}$ alkoxy; or cyclohexyl, 3-dimethylaminopropyl, or N-morpholinoethyl).
**Acyl azides can also rearrange to isocyanates.

The choice of the reactive group used to attach the dye to a substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten, such as biotin.

Although some selectivity can be obtained by careful control of the reaction conditions, selectivity of labeling is best obtained by selection of an appropriate reactive dye.

Typically, the reactive group, RG, will react with an amine, a thiol, an alcohol, an aldehyde or a ketone. Preferably, RG reacts with an amine or a thiol functional group. In one embodiment, RG is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. Nos. 5,580,990; 5,714,327; 5,985,566, incorporated herein by reference.

Where RG is an activated ester of a carboxylic acid, the reactive dye is particularly useful for preparing dye-conjugates of proteins, nucleotides, oligonucleotides, or haptens. Where RG is a maleimide or haloacetamide the reactive dye is particularly useful for conjugation to thiol-containing substances. Where RG is a hydrazide, the reactive dye is particularly useful for conjugation to periodate-oxidized carbohydrates and glycoproteins, and, in addition, is an aldehyde-fixable polar tracer for cell microinjection. Preferably, RG is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, RG is a succinimidyl ester of a carboxylic acid, a maleimide, an iodoacetamide, or a reactive platinum complex.

Alternatively, the reactive group, RG, is a photoactivatable group, such as an azide, diazirinyl, azidoaryl, or psoralen derivative, in which case the dye becomes chemically reactive only after illumination with light of an appropriate wavelength.

Synthesis of Reactive Dyes

Figure 1B:
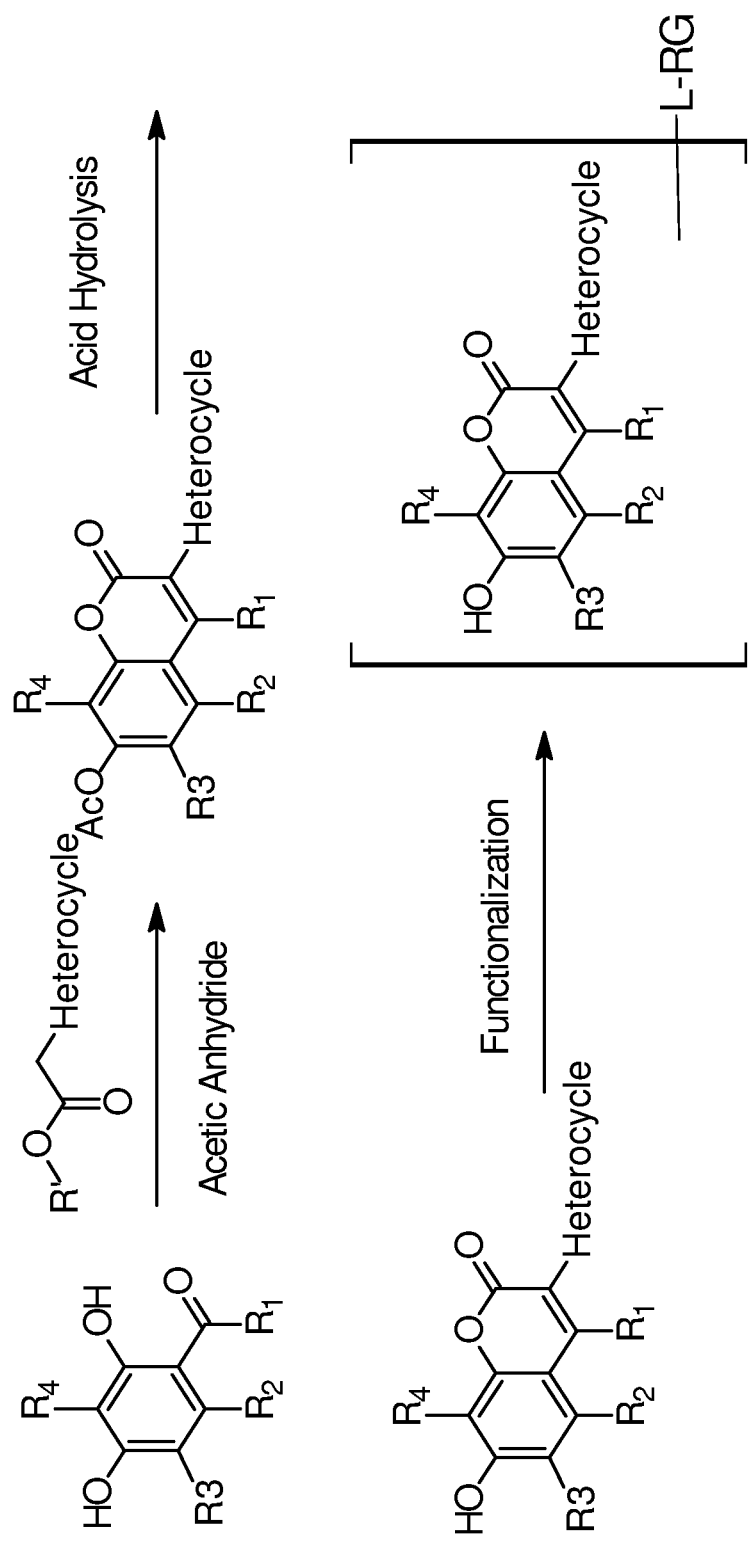
Figure 2:
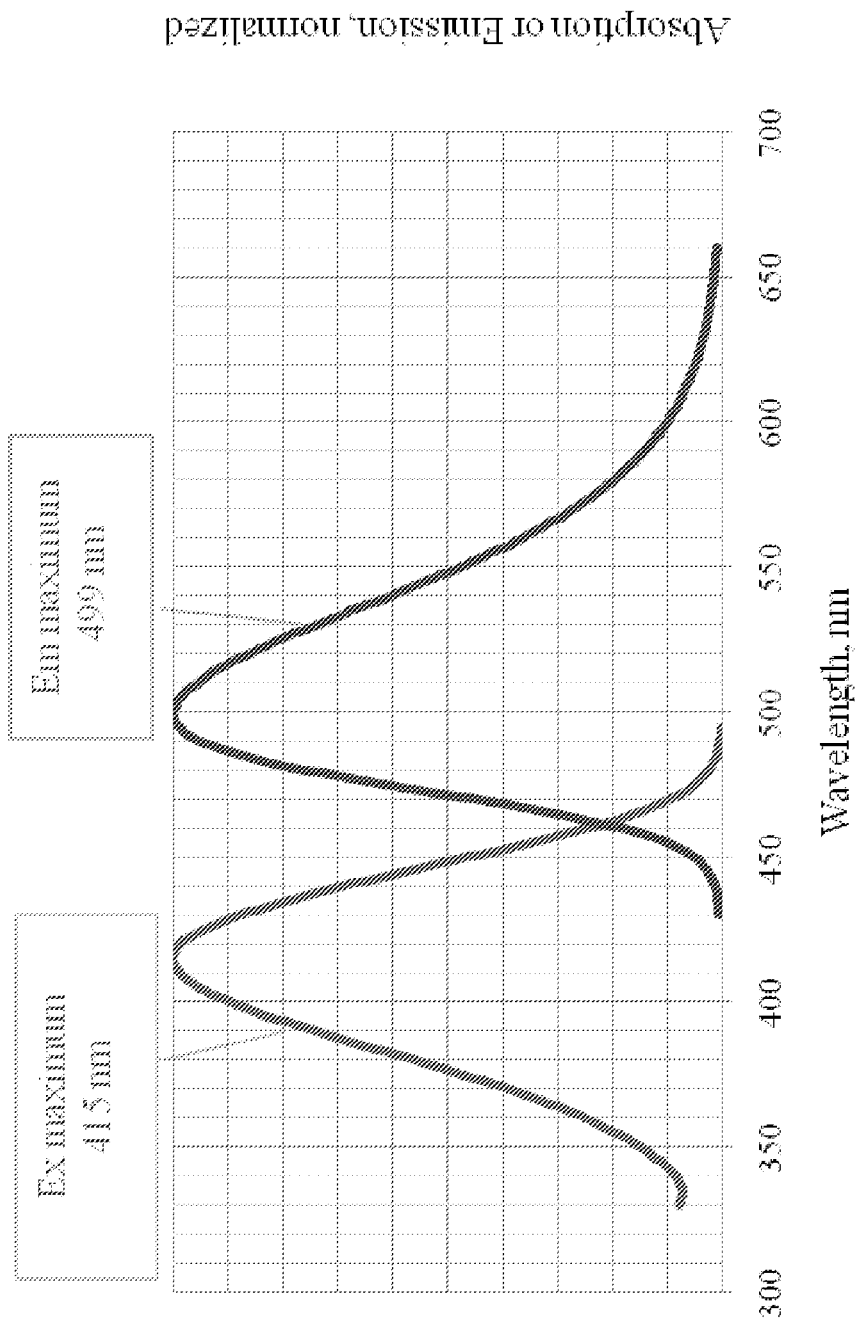
FIG. 2 shows the absorption and emission spectra of Compound 7 in pH=9.0 buffer. Compound 7 has its maximum absorption around 414 nm, which matches very well the 405 nm violet laser excitation of a typical flow cytometer.

The water-soluble, heterocycle-substituted 7-hydroxyl coumarins of the invention are either prepared from the acetic anhydride-based condensation of 4-carbonylresorcinols with a heterocycle acetatic acid or the base-catalyzed condensation of 4-carbonylresorcinols with active methylene compounds. These basic structures are optionally further substituted, during or after synthesis, to give the corresponding coumarin dye substituents, as defined above. It is recognized that there are many possible variations that may yield an equivalent results. The typical syntheses of the reactive coumarin dyes of the invention are illustrated in FIG. 1. Other known synthetic methods of comarins in the literature might be adapted to prepare the chemically reactive coumarins of the invention by certain modifications known to the ones skilled in the arts (see, for example, Bentsen et al., U.S. Pat. No. 6,566,508; Dittmer et al. 2005, J. Org. Chem. 70:4682; Shi et al., 2005, Fen Xi Hua Xue 33:1452; Sivakumar et al., 2004, Org. Lett 6:4603; Zhao et al., 2004, J. Am. Chem. Soc. 126:4653; Huang et al., 1994, J. Chem. Soc. Perkin Trans. 1: 102; and Kuznetsova and Kaliya, 1992, Russ. Chem. Rev. 61: 1243; each of which is incorporated herein by reference).

Methods for the synthesis of dyes containing a reactive group are well documented in the art. Amine-reactive dyes, such as "activated esters" of carboxylic acids, are typically synthesized by coupling a carboxylic acid to a relatively acidic "leaving group". Other preferred amine-reactive groups include sulfonyl halides, which are prepared from sulfonic acids using a halogenating agent such as PCl$_5$ or POCl$_3$; halotriazines, which are prepared by the reaction of cyanuric halides with amines; and isocyanates or isothiocyanates, which are prepared from amines and phosgene or thiophosgene, respectively.

Dyes containing amines and hydrazides, which are particularly useful for conjugation to carboxylic acids, aldehydes and ketones, are most often synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

Dye Conjugates

The reactive water-soluble, heterocycle-substituted 7-hydroxyl coumarin dyes of the invention can react with a wide variety of organic or inorganic substances (referred to herein as "substrates") that contain or are modified to contain functional groups with suitable reactivity, resulting in conjugation of the dye to the substance. Useful dye-conjugates include, among others, conjugates where the substrate is an amino acid, a nucleotide, a biopolymer (e.g., amino acid polymer, nucleic acid polymer, polysaccharide, carbohydrate, or lipid), an antigen, steroid, vitamin, drug, hapten, metabolite, toxin, environmental pollutant, ion-complexing moiety, or a glass, plastic, or other non-biological polymer. In some embodiments, the substrate is a cell, cellular system, cellular fragment or component, or subcellular particle (e.g., a virus particle, bacterial particle, or a component thereof). Reactive dyes typically label functional groups at the cell surface, in cell membranes, organelles, or cytoplasm.

For use in biological assays, the substrate typically is an amino acid, a nucleotide, or a biopolymer, such as an amino acid polymer, a nucleic acid polymer, a carbohydrate, or a polysaccharide. Dye-polymer conjugates can be prepared that incorporate a plurality of dye molecules conjugated to the substrate to increase the fluorescent signal from the dye-conjugate.

In one embodiment, substrate is an amino acid or an amino acid polymer, such as a peptide or protein. Examples of amino acid polymers usable in the present invention include, but are not limited to, antibodies (as broadly defined, above), IgG-binding proteins (e.g., protein A, protein G, protein A/G, etc.), enzymes, lectins, glycoproteins, histones, albumins, lipoproteins, avidin, streptavidin, protein A, protein G, phycobiliproteins and other fluorescent proteins, hormones, toxins, chemokines, growth factors, neuropeptides, cytokines, toxins, protease substrates, and protein kinase substrates. In a preferred embodiment, the biopolymer substrate is a monoclonal antibody.

In another embodiment, substrate is a nucleic acid base, nucleoside, nucleotide or a nucleic acid polymer. Nucleic acid polymers include those that are modified to possess an additional linker or spacer for attachment of the dyes of the invention, such as an alkynyl linkage (U.S. Pat. No. 5,047,519), an aminoallyl linkage (U.S. Pat. No. 4,711,955), a heteroatom-substituted linker (U.S. Pat. No. 5,684,142), or other linkage. In another embodiment, the conjugated substance is a nucleoside or nucleotide analog that links a purine or pyrimidine base to a phosphate or polyphosphate moiety through a noncyclic spacer. In another embodiment, the dye is conjugated to the carbohydrate portion of a nucleotide or nucleoside, typically through a hydroxyl group but alternatively through a thiol or amino group (e.g., as described in U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna et al., 2000, Proc Natl Acad Sci 97: 686-691.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen et al U.S. Pat. No. 5,539,082) may be preferred for some applications because of their generally faster hybridization rates.

In another embodiment, substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

In another embodiment, substrate is a lipid (typically having 6-60 carbons), including glycolipids, phospholipids, sphingolipids, and steroids. Alternatively, the conjugated substance is a lipid assembly, such as a liposome. The lipophilic moiety may be used to retain the conjugated substances in cells, as described in U.S. Pat. No. 5,208,148. Certain polar dyes of the invention may also be trapped within lipid assemblies.

Conjugates in which the substrate is an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517, 5,516,911, and 5,049,673); derivatives of 2-carboxymethoxyaniline-N,N-di-acetic acid (APTRA chelators; Am. J. Physiol. 256, C540 (1989)); or pyridine- and phenanthroline-based metal ion chelators (U.S. Pat. No. 5,648,270); or derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan et al., 1996, Anal Biochem 236:101-106. Preferably, the ion-complexing moiety is a crown ether chelator, a BAPTA chelator, an APTRA chelator or a derivative of nitrilotriacetic acid.

Other conjugates of non-biological materials include dye-conjugates of organic or inorganic polymers, polymeric films, polymeric wafers, polymeric membranes, polymeric particles, or polymeric microparticles; including magnetic and non-magnetic microspheres; iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations.

In some embodiments, dye-conjugates are further labeled with at least one second luminescent dye, which is optionally an additional dye of the present invention, to form an energy-transfer pair. In some aspects of the invention, the labeled conjugate functions as an enzyme substrate, and enzymatic hydrolysis disrupts the energy transfer.

The fluorescent dye-conjugates, particularly wherein the substrate is biopolymer, can incorporate multiple dyes per substrate molecule to increase the fluorescent signal. Preferably, at least 3 molecules of dyes are incorporated into dye-biopolymer conjugates. In embodiments in which the biopolymer is an antibody, at least three, more preferably at least 6 dye molecules are conjugated to the antibody. In some embodiments, as many as about 35 dye molecules can be conjugated to the antibody without significant self-quenching, but more typically as many as about 15-20. It will be understood by one of skill in the art that each stated range of dyes per conjugate substrate is intended to describe all values within the range. Thus, for example, by stating that fluorescent biopolymers of the intention contain 6-15 dye molecules, biopolymers containing 6, 7, 8, . . . , or 15 dye molecules are also part of the invention.

Preparation of Dye-Conjugates

The fluorescent dye-conjugates of the present invention typically are synthesized as the product of a reaction between a substrate and a reactive water-soluble, heterocycle-substituted 7-hydroxycoumarin dye. The preparation of dye conjugates using reactive dyes is well documented, e.g., Hermanson, 1996, Biocojugate Techniques (Academic Press, New York, N.Y.); Haugland, 1995, Methods Mol. Biol. 45:205-21; and Brinkley, 1992, Bioconjugate Chemistry 3:2, each incorporated herein by reference. Conjugates typically result from mixing appropriate reactive dyes and the substance to be conjugated in a suitable solvent in which both are soluble. Aqueous solutions of the reactive water-soluble, heterocycle-substituted 7-hydroxycoumarin dyes described herein are readily created, facilitating conjugation reactions with most biological materials. For those reactive dyes that are photoactivated, conjugation requires illumination of the reaction mixture to activate the reactive dye.

The fluorescent biopolymers of the present invention typically are synthesized as the product of a reaction between a biopolymer and a reactive water-soluble, heterocycle-substituted 7-hydroxyl coumarin, wherein the reaction conditions result in the conjugation of multiple dye molecules to each biopolymer. Alternatively, the fluorescent biopolymer can be synthesized as a polymerization reaction of subunit molecules, wherein one or more of the subunit molecules have been conjugated to a reactive water-soluble, heterocycle-substituted 7-hydroxyl coumarin prior to polymerization of the biopolymer. An example of the latter method is the synthesis of oligonucleotides using standard phosphoramidite chemistry, where at least one phosphoramidite is dye-labeled.

Applications and Methods of Use

In one aspect of the invention, the reactive dyes of the invention are used to directly stain or label a sample, or components of the sample, so that the sample can be identified or quantitated. Chemically reactive dye compounds will covalently attach to a corresponding functional group on a wide variety of materials, forming dye conjugates, as described above.

In preferred embodiments, the reactive dye compounds of the intention are used to directly stain or label samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the typical concentrations of use.

For direct staining, the dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

Dyes that incorporate an aliphatic amine or a hydrazine residue can be microinjected into cells, where they can be fixed in place by aldehyde fixatives such as formaldehyde or glutaraldehyde. This fixability makes such dyes useful for intracellular applications such as neuronal tracing.

Dye compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

For direct staining of analytes in biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence are accomplished.

In another aspect of the invention, the fluorescent dye-conjugates of the present invention are useful as, or as part of, detection reagents, typically analyte-specific detection reagents, to facilitate the optical detection and analysis of analytes. In one embodiment, the dye-conjugate substrate itself is an analyte-specific reagent, and the fluorescent dye-conjugate is used as a detection reagent to label an analyte of interest. In an alternative embodiment, the fluorescent dye-conjugate is bound to an analyte-specific reagent, and the combined entity is used as detection reagents to label an analyte of interest. In this alternative embodiment, the dye-conjugate acts as a fluorescent label bound to the analyte-specific reagent.

Assays in which one or more analytes of interest are labeled using analyte-specific detection reagents and subsequently optically analyzed are well known in the art, and the present fluorescent dye-conjugates are generally useful as detection reagents in such assays. For example, proteins in a sample can be labeled using a detection reagent consisting of a labeled protein, typically an antibody, that binds specifically to the analyte protein. Detection of the resulting labeled analyte proteins can be carried out using a number of well known assay formats and instrumentation, including using flow cytometry, scanning cytometry, imaging, and gel analysis. Flow cytometry is described at length in the extensive literature in this field, including, for example, Landy et al. (eds.), Clinical Flow Cytometry, Annals of the New York Academy of Sciences Volume 677 (1993); Bauer et al. (eds), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed), Handbook of Biological Confocal Microscopy, 2nd Edition, Plenum Press (1989), incorporated herein by reference.

Illumination sources useful for exciting the fluorescent polymers of the invention include, but are not limited to, hand-held ultraviolet lamps, mercury arc lamps, xenon lamps, lasers and laser diodes. These illumination sources are optionally integrated into laser scanners, fluorescence microplate readers, standard or mini-fluorometers, or chromatographic detectors. Preferred fluorescent polymers of the invention are excitable at or near 405 nm, and can be excited using a relatively inexpensive violet laser excitation source.

Kits

One aspect of the instant invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates, or present as a dye-conjugate where the conjugated substance is a specific binding pair member, or a nucleoside, nucleotide, oligonucleotide, nucleic acid polymer, peptide, or protein. The kits optionally further comprise one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

EXAMPLES

Examples of the synthesis strategies of selected dyes, the synthesis of selected fluorescent biopolymers, their characterization, and methods of use are provided in the examples below. Further modifications and permutations will be obvious to one skilled in the art. The examples below are given so as to illustrate the practice of this invention, and are not intended to limit or define the entire scope of the invention.

Example 1

Preparation of Compound 1

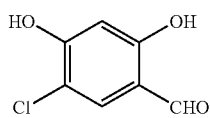

Compound 1

4-Chlororesorcinol (50 g) is dissolved in dry ether (200 ml). To the solution are added finely powdered zinc cyanide (60 g) and potassium chloride (12 g) with stirring. The suspension is cooled to 0° C. A strong stream of hydrogen chloride gas is blown into the solution with vigorous stirring. After approximately 30-60 minutes the reactants are dissolved. The addition of hydrogen chloride gas is continued until it stops being absorbed in the ether solution. The suspension is stirred for one additional hour on ice. The ether solution is poured from the solid that is treated with ice and heated to 100° C. in a water bath. Upon cooling the product crystallized in shiny plates from the solution, which is removed by filtration and air-dried to give the desired aldehyde.

Example 2

Preparation of Compound 2

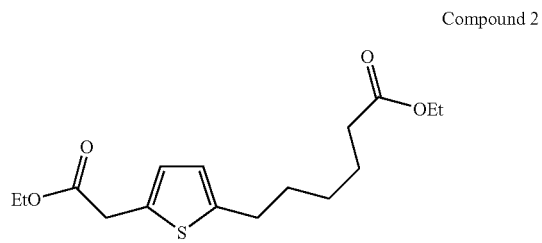 [SMILES: CCOC(=O)CCCCCc1ccc(CC(=O)OCC)s1]

Compound 2

Ethyl 2-thiopheneneacetate (10 g) and ethyl 6-bromohexanoate (12 g) are dissolved in dichloromethane (200 ml). To the solution is added anhydrous $AlCl_3$ (24 g) under dry nitrogen protection with vigorous stirring at 0° C. The reaction mixture is stirred under dry nitrogen protection at 0° C., and warmed to room temperature when the reaction is complete as indicated by TLC. The reaction mixture is poured into ice-water, and extracted with chloroform (3×200 ml). The chloroform layers are combined, dried over anhydrous $Na_2SO_4$, and the solvent is removed under vacuum to give a crude solid. The crude solid is further purified on a silica gel column with a gradient of chloroform/ethyl acetate as eluant to yield the desired Compound 2.

Example 3

Preparation of Compound 3

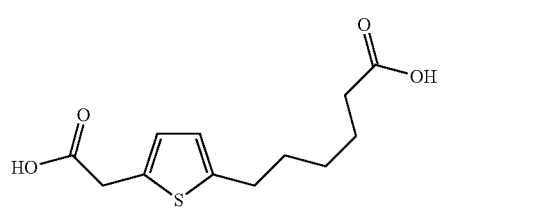

Compound 3

Compound 2 (10 g) is dissolved in ethanol (100 ml). To the solution is added 5 M NaOH (65 ml). The reaction mixture is stirred at room temperature, and neutralized with concentrated HCl when the reaction is complete as indicated by TLC. The resulted mixture is extracted with ethyl acetate (3×200 ml). The ethyl acetate layers are combined, dried over anhydrous $Na_2SO_4$, and the solvent is removed under vacuum to give the desired Compound 3.

Example 4

Preparation of Compound 4

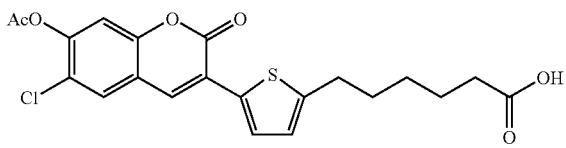

Compound 4

Compound 1 (6 g) and Compound 3 (5.8 g) are suspended in acetic anhydride (100 ml). To the suspension, triethylamine (6 ml) is added at room temperature. The reaction mixture is heated at 120-140° C. until the reaction is complete as indicated by TLC. After cooling to room temperature, the mixture is poured into ice-water, and resulted precipitate is filtered off with suction to collect the solid that is air-dried. The crude product is recrystallized to yield the desired Compound 4.

Example 5

Preparation of Compound 5

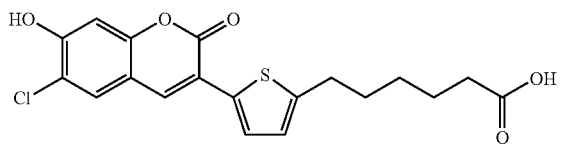

Compound 5

Compound 4 (5 g) is suspended in 20% HCl (300 ml). The reaction mixture is heated at 60-70° C. until the reaction is complete as indicated by TLC. The reaction mixture is diluted with water (200 ml), and extracted with ethyl acetate (3×300 ml). The ethyl acetate layers are combined, dried over anhydrous $Na_2SO_4$, and the solvent is removed under vacuum to give the crude Compound 5. The crude material is further purified on a silica gel column with a gradient of chloroform/methanol as eluant to yield the desired Compound 5.

Example 6

Preparation of Compound 6

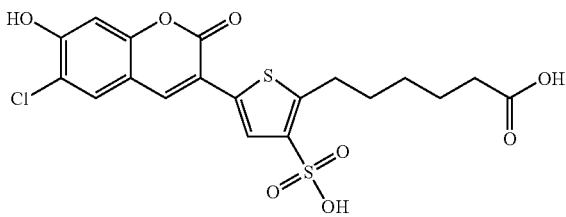

Compound 6

Compound 5 (1 g) is suspended in concentrated $H_2SO_4$ (5 ml). To the suspension is added 20% fuming $H_2SO_4$ (5 ml). The reaction mixture is stirred at 0° C. until the reaction is complete as indicated by TLC. To cold ether (200 ml), the reaction mixture is drop-wise added with vigorous stiffing to give the crude Compound 6 as a yellow precipitate. The crude material is further purified by preparative HPLC to yield the desired Compound 6 using 0.1% TFA in water-0.1% TFA in a MeCN buffer system.

Example 7

Preparation of Compound 7

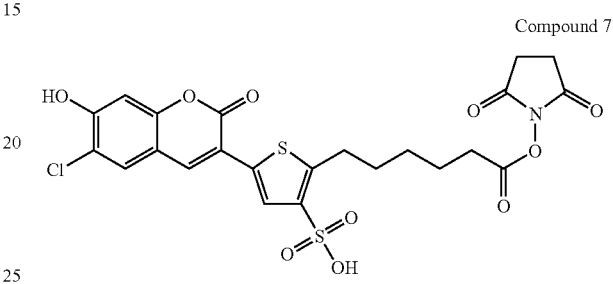

Compound 7

Compound 6 (100 mg) and N,N'-disuccinimidyl carbonate (85 mg) are dissolved in DMF (5 ml). To the solution is added 4-dimethylaminopyridine (5 mg) and anhydrous triethylamine (0.1 ml) under dry nitrogen protection with vigorous stiffing at room temperature. The reaction mixture is stirred under dry nitrogen protection at room temperature until the reaction is complete as indicated by TLC. The reaction mixture is poured into ether, and the resulted precipitate is collected by filtration. The solid is washed with ether to yield the desired Compound 7.

Example 8

Preparation of Compound 8

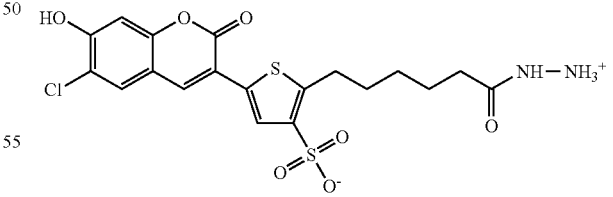

Compound 8

To anhydrous hydrazine (100 µl) in DMF (0.5 ml) is added Compound 7 (100 mg) in DMF (0.5 ml). The mixture is stirred at ambient temperature for 15 minutes. The reaction solution is poured into water, and resulted precipitate is centrifuged to collect the solid that is washed with water and air-dried. The crude product is further purified by HPLC.

Example 9

Preparation of Compound 9

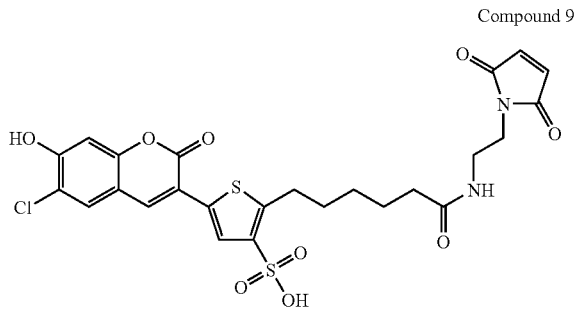 [SMILES: O=C(CCCCCc1sc(-c2cc3cc(Cl)c(O)cc3oc2=O)cc1S(=O)(=O)O)NCCN1C(=O)C=CC1=O]

Compound 9

To Compound 7 (10 mg) in DMF (0.2 ml) at room temperature is added 4 equivalents of triethylamine and 1.2 equivalents of N-(2-aminoethyl)maleimide, trifluoroacetic acid salt (Sigma-Aldrich). The mixture is stirred at ambient temperature for 60 minutes. The DMF solution is poured into water, and resulted suspension is centrifuged to collect the solid that is air-dried. The crude product is further purified with silica gel chromatography to yield the desired Compound 9.

Example 10

Preparation of Compound 10

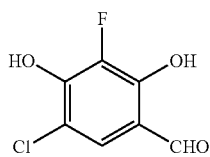

Compound 10

Compound 10 is prepared from 4-chloro-2-fluororesorcinol (Fanbo Biochemicals, Ltd., Beijing, China), analogous to the procedure for preparing Compound 1.

Example 11

Preparation of Compound 11

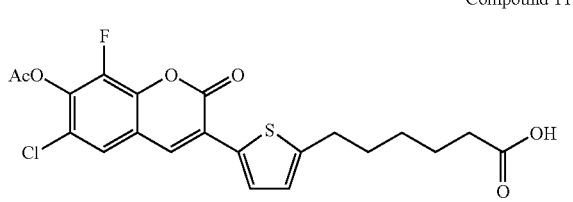

Compound 11

Compound 11 is prepared from the condensation of Compound 10 with Compound 3, analogous to the procedure for preparing Compound 4.

Example 12

Preparation of Compound 12

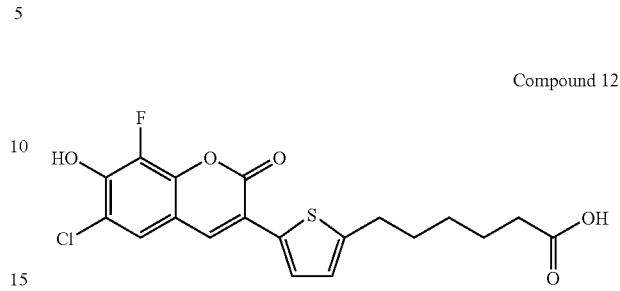

Compound 12

Compound 12 is prepared from the acidic hydrolysis of Compound 11 with 20% HCl, analogous to the procedure for preparing Compound 5.

Example 13

Preparation of Compound 13

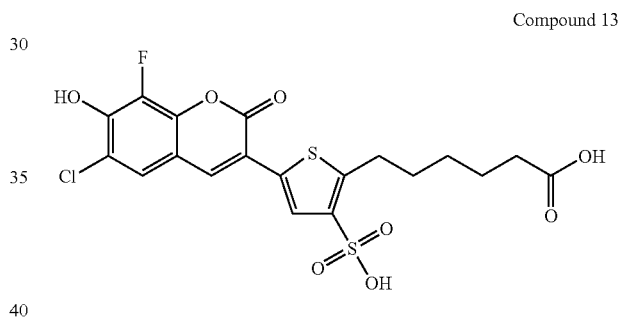

Compound 13

Compound 13 is prepared from the sulfonation of Compound 12, analogous to the procedure for preparing Compound 6.

Example 14

Preparation of Compound 14

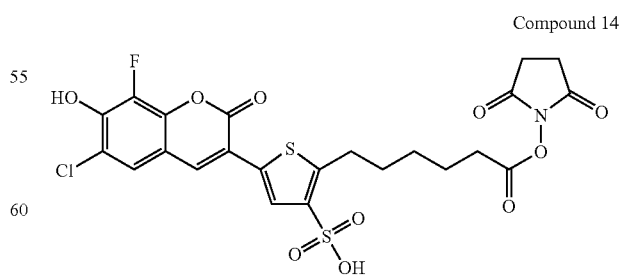

Compound 14

Compound 14 is prepared from the condensation of Compound 13 with N,N'-disuccinimidyl carbonate, analogous to the procedure for preparing Compound 7.

Example 15

Preparation of Compound 15

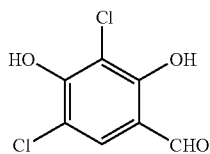

Compound 15

Compound 15 is prepared from 2,4-dichlororesorcinol (Fanbo Biochemicals, Ltd.), analogous to the procedure for preparing Compound 1.

Example 16

Preparation of Compound 16

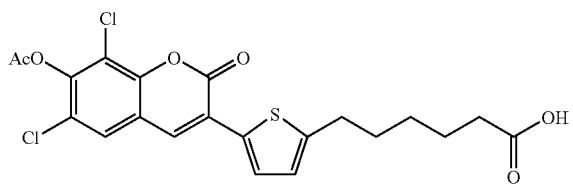

Compound 16

Compound 16 is prepared from the condensation of Compound 15 with Compound 3, analogous to the procedure for preparing Compound 4.

Example 17

Preparation of Compound 17

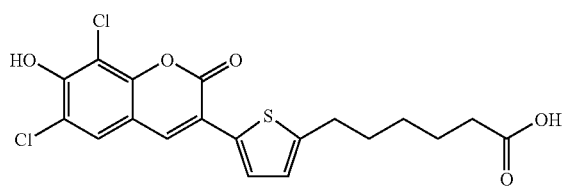

Compound 17

Compound 17 is prepared from the acidic hydrolysis of Compound 16 with 20% HCl, analogous to the procedure for preparing Compound 5.

Example 18

Preparation of Compound 18

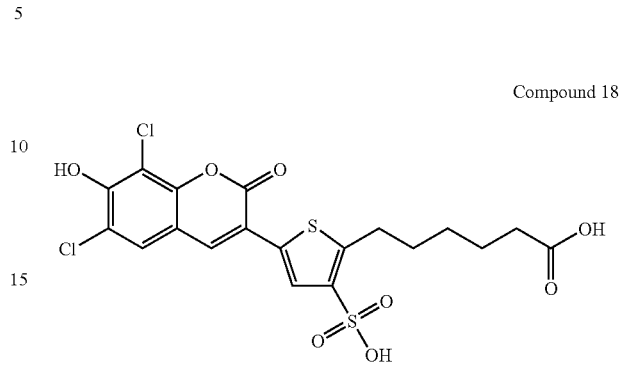

Compound 18

Compound 18 is prepared from the sulfonation of Compound 17, analogous to the procedure for preparing Compound 6.

Example 19

Preparation of Compound 19

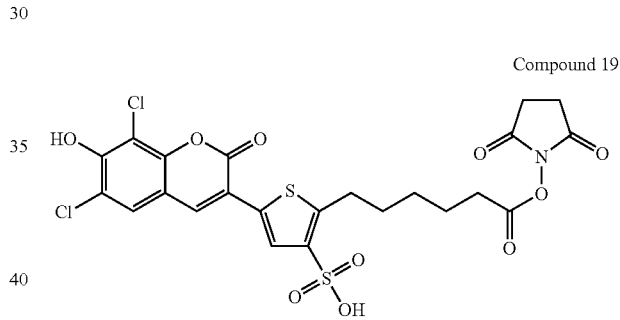

Compound 19

Compound 19 is prepared from the condensation of Compound 18 with N,N'-disuccinimidyl carbonate, analogous to the procedure for preparing Compound 7.

Example 20

Preparation of Compound 20

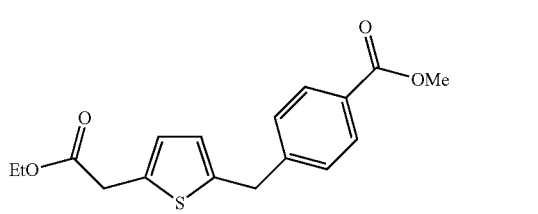

Compound 20

Ethyl 2-thiopheneneacetate (5 g) and methyl 4-bromomethylbenzoate (6.2 g) are dissolved in dichloromethane (200 ml). To the solution is added anhydrous AlCl$_3$ (12 g) under dry nitrogen protection with vigorous stiffing at 0° C. The reaction mixture is stirred under dry nitrogen protection at 0° C., and warmed to room temperature when the reaction is complete as indicated by TLC. The reaction mixture is poured into ice-water, and extracted with chloroform (3×200 ml). The chloroform layers are combined, dried over anhydrous Na$_2$SO$_4$, and the solvent is removed under vacuum to give a crude solid. The crude solid is further purified on a silica gel column with a gradient of hexanes/ethyl acetate as eluant to yield the desired Compound 20.

Example 21

Preparation of Compound 21

Compound 21

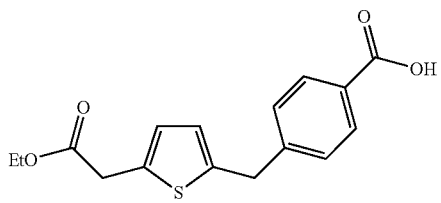

Compound 20 (5 g) is dissolved in ethanol (50 ml). To the solution is added 5 M NaOH (65 ml). The reaction mixture is stirred at room temperature, and neutralized with concentrated HCl when the reaction is complete as indicated by TLC. The reaction mixture is extracted with ethyl acetate (3×200 ml). The ethyl acetate layers are combined, dried over anhydrous Na$_2$SO$_4$, and the solvent is removed under vacuum to give the desired Compound 21.

Example 22

Preparation of Compound 22

Compound 22

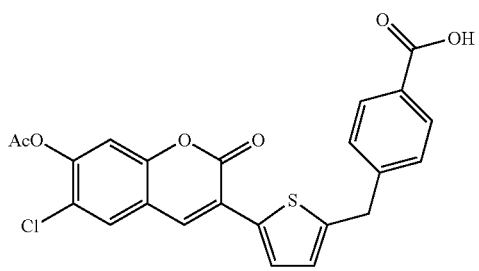

Compound 22 is prepared from the condensation of Compound 21 with Compound 1, analogous to the procedure for preparing Compound 4.

Example 23

Preparation of Compound 23

Compound 23

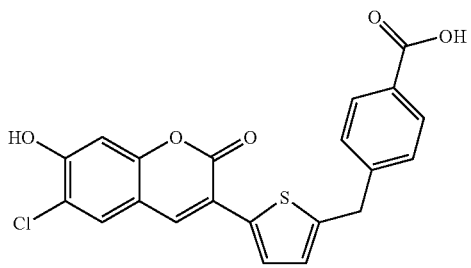

Compound 23 is prepared from the acidic hydrolysis of Compound 22 with 20% HCl, analogous to the procedure for preparing Compound 5.

Example 24

Preparation of Compound 24

Compound 24

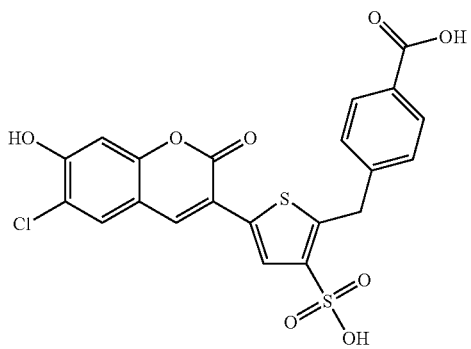

Compound 24 is prepared from the sulfonation of Compound 23, analogous to the procedure for preparing Compound 6.

Example 25

Preparation of Compound 25

Compound 25

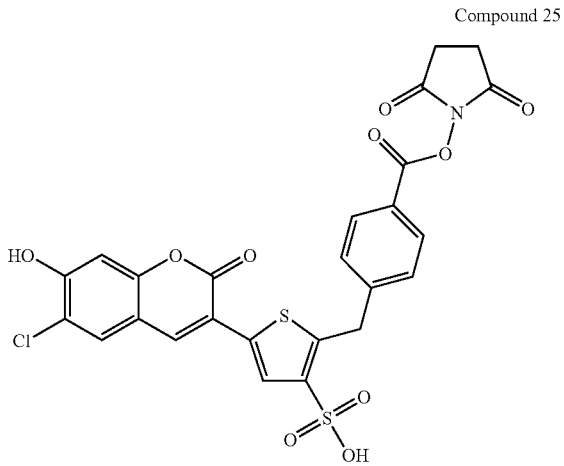 [SMILES: O=C(ON1C(=O)CCC1=O)c1ccc(Cc2sc(-c3cc4cc(Cl)c(O)cc4oc3=O)cc2S(=O)(=O)O)cc1]

Compound 25 is prepared from the condensation of Compound 24 with N,N'-disuccinimidyl carbonate, analogous to the procedure for preparing Compound 7.

Example 26

Preparation of Compound 26

Compound 26

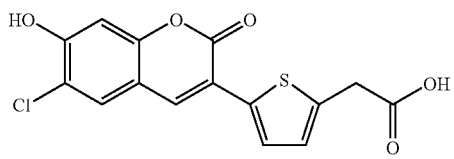

Compound 1 (1 g) and 2,5-dicarboxymethylthiophene (6 g, Sigma-Aldrich) are suspended in acetic anhydride (100 ml). To the suspension triethylamine (6 ml) is added at room temperature. The resulted reaction mixture is heated at 120-140° C. until the reaction is complete as indicated by TLC. After cooling to room temperature, the mixture is poured into ice-water, and resulted precipitate is filtered off with suction to collect the solid that is air-dried. The crude solid is further purified on a silica gel column with a gradient of chloroform/methanol as eluant to yield the desired Compound 26.

Example 27

Preparation of Compound 27

Compound 27

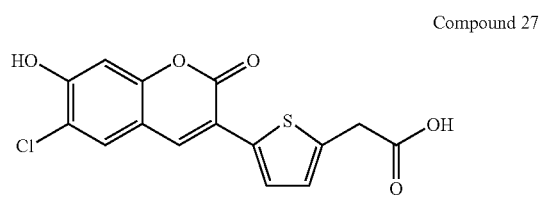 [SMILES: O=C(O)Cc1ccc(-c2cc3cc(Cl)c(O)cc3oc2=O)s1]

Compound 27 is prepared from the acidic hydrolysis of Compound 26 with 20% HCl, analogous to the procedure for preparing Compound 5.

Example 28

Preparation of Compound 28

Compound 28

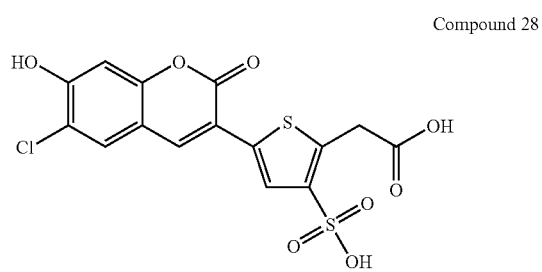 [SMILES: O=C(O)Cc1sc(-c2cc3cc(Cl)c(O)cc3oc2=O)cc1S(=O)(=O)O]

Compound 28 is prepared from the sulfonation of Compound 27, analogous to the procedure for preparing Compound 6.

Example 29

Preparation of Compound 29

Compound 29

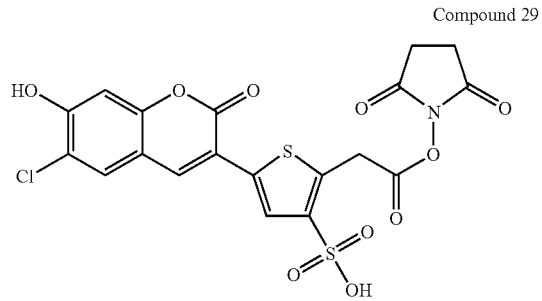 [SMILES: O=C(Cc1sc(-c2cc3cc(Cl)c(O)cc3oc2=O)cc1S(=O)(=O)O)ON1C(=O)CCC1=O]

Compound 29 is prepared from the condensation of Compound 24 with N,N'-disuccinimidyl carbonate, analogous to the procedure for preparing Compound 7.

Example 30

Preparation of Compound 30

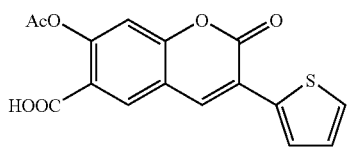

Compound 30

Compound 30 is prepared from the condensation of 2,4-dihydroxy-5-formylbenzoic acid (Fanbo Biochemicals, Ltd.) with 2-thiopheneacetic acid, analogous to the procedure for preparing Compound 4.

Example 31

Preparation of Compound 31

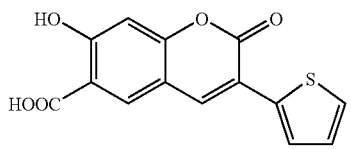

Compound 31

Compound 31 is prepared from the acidic hydrolysis of Compound 30 with 20% HCl, analogous to the procedure for preparing Compound 5.

Example 32

Preparation of Compound 32

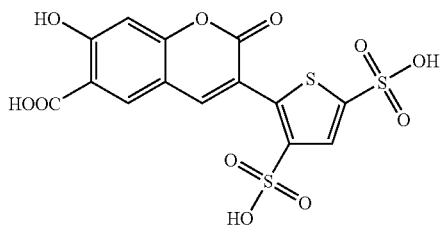

Compound 32

Compound 32 is prepared from the sulfonation of Compound 31, analogous to the procedure for preparing Compound 6.

Example 33

Preparation of Compound 33

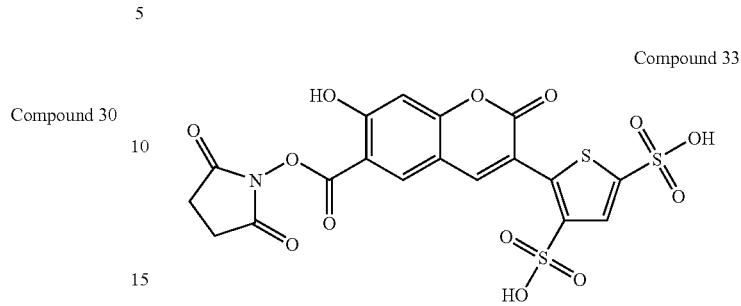

Compound 33

Compound 33 is prepared from the condensation of Compound 32 with N,N'-disuccinimidyl carbonate, analogous to the procedure for preparing Compound 7.

Example 34

Preparation of Compound 34

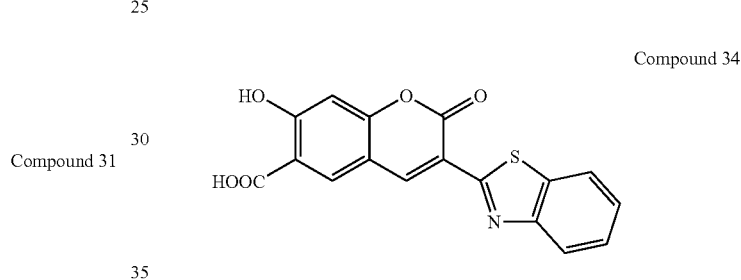

Compound 34

Ethyl 2-benzothiazoleacetate (5 g, Sigma-Aldrich), 2,4-dihydroxy-5-formylbenzoic acid (2 g, Fanbo Biochemicals, Ltd.), 0.5 ml of piperidine and 0.3 ml of acetic acid are heated under reflux in 100 ml of methanol until the reaction is complete as indicated by TLC. After cooling to room temperature, the mixture is filtered and the filtrate is concentrated. The concentrated filtrated is poured into water, and resulted precipitate is filtered off with suction to collect the solid that is air-dried. The crude product is further purified with silica gel chromatography to yield the desired Compound 34.

Example 35

Preparation of Compound 35

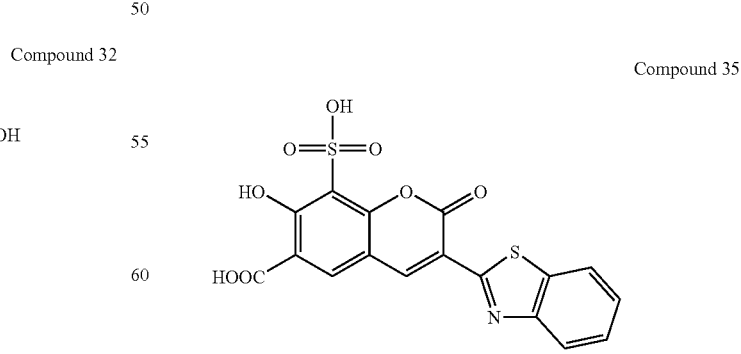

Compound 35

Compound 35 is prepared from the sulfonation of Compound 34, analogous to the procedure for preparing Compound 6.

Example 36

Preparation of Compound 36

*Compound 36*

Compound 36 is prepared from the condensation of Compound 35 with N,N'-disuccinimidyl carbonate, analogous to the procedure for preparing Compound 7.

Example 37

Preparation of Compound 37

*Compound 37*

Methyl 4-carboxymethylpyridine (5 g) and methyl 6-bromohexanoate (8 g) are heated in 1,2-dichlorobenzene (50 ml) until the reaction is complete as indicated by TLC. After cooling to room temperature, the mixture is filtered to collect the solid that is washed with ether and air-dried. The crude product is directly used for next step reaction without further purification.

Example 38

Preparation of Compound 38

*Compound 38*

Compound 38 is prepared from the piperidine-catalyzed condensation of Compound 37 with resorcinol, analogous to the procedure for preparing Compound 34.

Example 39

Preparation of Compound 39

*Compound 39*

Compound 39 is prepared from the hydrolysis of Compound 38, analogous to the procedure for preparing Compound 5.

Example 40

Preparation of Compound 40

*Compound 40*

Compound 40 is prepared from the condensation of Compound 39 with N,N'-disuccinimidyl carbonate, analogous to the procedure for preparing Compound 7.

Example 41

Preparation of Protein-Dye Conjugates

Protein-dye conjugates can be prepared by standard means, such as those described in, for example, Haugland et al. 1995, Meth. Mol. Biol. 45:205; Haugland, 1995, Meth. Mol. Biol. 45:223; Haugland, 1995, Meth. Mol. Biol. 45:235; Haugland, 2000, Current Protocols In Cell Biology 16.5.1-16.5.22; each of which is incorporated herein by reference. For example, protein-dye conjugates can be prepared using a succinimidyl ester of the invention, as follows.

A solution of the protein is prepared at about 10 mg/mL in 0.1 M sodium bicarbonate. The labeling reagents are dissolved in a suitable solvent such as water, or DMF or DMSO at about 10 mg/mL. Predetermined amounts of the labeling reagents are added to the protein solutions with stiffing. The reaction mixture is incubated at room temperature for one hour or on ice for several hours. The dye-protein conjugate is typically separated from free unreacted reagent by size-exclusion chromatography, such as on Amersham PD-10 resin (GE Healthcare Bio-Sciences Corp., Piscataway, N.J.) equilibrated with phosphate-buffered saline (PBS). The initial, protein-containing colored band is collected and the degree of substitution is determined from the absorbance at the absorbance maximum of each fluorophore, using the extinction coefficient of the free fluorophore. The dye-protein conjugate thus obtained can be subfractionated to yield conjugates with higher, lower or more uniform DOS.

For many applications, such as for producing dye-labeled antibodies, a molar ratio of 10 to 50 equivalents of dye to 1 equivalent of protein is used. It will be understood that optimal reaction conditions and reactant concentrations typically are determined empirically. Optimization of dye-protein conjugation is well known in the art, and described in, for example, the references cited herein.

Example 42

Preparation of Antibody-Dye Conjugates

A preferred protocol for preparing dye-conjugates of an IgG monoclonal antibody is described below. Dye-conjugates of Compounds 7, 13, 14, 19, 25, and 60 were prepared using essentially the sample protocol, with minor variations, as noted below.

Step 1. Prepare antibody solution: Prepare a solution of the antibody in labeling buffer (0.05M NaPi, pH 8.0+0.15M NaCl+20% glycerol) at a concentration of about 2-20 mg/ml.

The concentration of the antibody in solution can be calculated from the Beer-Lambert Law, $A_{280}=\epsilon_p \cdot C \cdot L$, where $A_{280}$ is the absorbance measured at 280 nm (which is the maximum absorption wavelength of protein), $\epsilon_p$ is the molar extinction coefficient of the antibody protein, C is the concentration, and L is the length of the light path through the solution. A typical IgG antibody has an $\epsilon_p$ value of 224,000 $cm^{-1}M^{-1}$.

Step 2. Prepare dye solution: A dye solution is prepared by dissolving the dye in DMSO. The concentration if the dye solution is determined as described below. The accuracy of the measurement of the dye concentration may be improved by first diluting the dye 1/100 in 1M glycine, pH 9.6.

The concentration of the dye in solution can be calculated from the Beer-Lambert Law: $A_{max}=\epsilon_{dye} \cdot C \cdot L$, were $A_{max}$ is the absorbance measured at the maximum absorption wavelength of the dye, $\epsilon_{dye}$ is the molar extinction coefficient of the dye, C is the concentration, and L is the length of the light path through the solution. As an example, the maximum absorption wavelength of the Compound 7 amide is about 415 nm. For other dye compounds, the maximum absorption wavelength of the reactive dye should be measured prior to the conjugation.

Step 3. Carry out conjugation reaction: Calculate amounts of the antibody and dye solutions to obtain the desired molar excess of dye in the reaction. For optimization studies, reactions are carried out using a range of molar excess of dye, typically between 2× and 60× molar excess of dye. Add the antibody solution to the dye solution with effective stirring or shaking, and keep the reaction mixture stirred or shaken for 1-2 hrs to obtain the antibody-dye conjugate.

Step 4. Purify the conjugate: The antibody-dye conjugate can be purified using Bio-Spin column. Load 500 of antibody-dye conjugate solution and 500 µl a chase buffer (PBS+20% glycerol+0.1% NaN$_3$) on a Bio-Spin column, place 1 ml of chase buffer into the receiver tube of the spin column, and separate. Vortex after separation.

Alternatively, the antibody-dye conjugate can be purified using a PD-10 column (Amersham Biosciences, Piscataway, N.J.), following the manufacturer's protocol.

Step 5. Determine the degree of substitution of the antibody-dye conjugate: The degree of substitution (DOS) is calculated using the following equation:

$$DOS=[dye]/[antibody]=A_{max} \cdot \epsilon_p/(\epsilon_{dye} \cdot (A_{280}-0.55 \cdot A_{max})),$$

where [dye] is the dye concentration, [antibody] is the antibody concentration, $A_{max}$ is the absorbance measured at the maximum absorption wavelength of the dye, $A_{280}$ is the absorbance measured at 280 nm, $\epsilon_p$ is the molar extinction coefficient of the antibody protein, $\epsilon_{dye}$ is the molar extinction coefficient of the dye. It should be noted that to obtain accurate DOS, the conjugate should be free of the non-conjugated dye.

For effective labeling, the degree of substitution typically should fall between 3-20 moles of dye to one mole of antibody. As is well known in the art, the DOS that provides optimal labeling will depend on the antibody, and in some cases, a higher DOS may provide improved labeling. The optimal labeling is determined empirically by preparing dye-conjugates over a range of DOS and comparing the measured fluorescence intensities. Examples are shown in the figures.

Example 43

Preparation of Dye-Conjugates of Periodate-Oxidized Glycoproteins

Samples of 5 mg of goat IgG antibody (which has a polysaccharide chain attached to the protein) in 1 mL of 0.1 M acetate, 0.135 M NaCl, pH 5.5, are treated with 2.1 mg of sodium metaperiodate on ice for a period of time experimentally determined to be sufficient to result in the desired amount of aldehyde groups on the glycoprotein, which are then reacted with Compound 5. The reactions are stopped by addition of 30 µL ethylene glycol. The antibodies are purified on a Sephadex G25 column packed in PBS pH 7.2. One-tenth volume of 1 M sodium bicarbonate is added to raise the pH and Compound 5 is added at a molar ratio of dye to protein of 50:1. The reaction is stirred at room temperature for a period of time experimentally determined to be sufficient to result in the desired dye/protein ratio. Sodium cyanoborohydride is added to a final concentration of 10 mM and the reaction is stirred for 4 hours at room temperature. The antibody conjugates are purified by dialysis and on Sephadex G25 columns as described above. Periodate-oxidized glycoproteins in gels and on blots can also be labeled, essentially as described in Estep and Miller, 1986, Anal. Biochem. 157:100-105, incorporated herein by reference.

Example 44

Preparation of a Protein-Dye Conjugate Using a Thiol-Reactive Dye

A solution of beta-galactosidase, a protein rich in free thiol groups, is prepared in PBS (2.0 mg in 400 µL). The protein solution is then treated with a 10 mg/L solution of the maleimide derivative Compound 9 in DMF. Unreacted dye is removed on a spin column. The degree of substitution by the dye is estimated using the extinction coefficient of the free dye, as described in Example 42. The protein concentration is estimated from the absorbance at 280 nm, corrected for the absorbance of Compound 9 at that wavelength.

Example 45

Preparation of Aminodextran-Dye Conjugates

Aminodextran-dye conjugates are prepared as follows, described using 70,000 MW aminodextran (50 mg) derivatized with an average of 13 amino groups as an example. The aminodextran (50 mg) is dissolved at 10 mg/mL in 0.1 M $NaHCO_3$. Compound 7, 13, 14, 19, or 60 is added so as to give a dye/dextran ratio of about 10-15. After 6-12 hours, the resulting conjugate is purified on SEPHADEX G-50 and eluted with water. Typically 6-10 moles of dye are conjugated to 70,000 MW dextran.

Example 46

Preparation of Dye-Labeled Microspheres

Microspheres can be labeled with a dye of the present invention using any of a number of well know protocols. Examples are described, below.

Microspheres chemically modified to have functional groups such as amino, carboxyl, or aldehydes on the surface can be surface-labeled by covalently conjugating the surface groups with a corresponding reactive dyes, as listed in Table 1. For example, amine-modified microspheres are readily conjugated to the dyes of the invention through succinimidyl esters, such as Compound 7, 13, 14, 19, 25 or 60.

A dye-labeled protein, prepared as described above, can be covalently coupled through its amine residues to carboxylate groups on a microsphere using ethyl 3-(dimethylaminopropyl)carbodiimide (EDAC). Alternatively, the dye-labeled protein can be passively adsorbed on the microspheres. For example, carboxylate-modified microspheres are suspended in a solution dye-labeled protein, the protein is allowed to passively adsorb on the microspheres, and excess protein is removed by centrifugation and washing. Microparticles of a size that cannot be centrifuged are separated from excess protein by dialysis through a semi-permeable membrane with a high MW cutoff or by gel filtration chromatography.

Biotinylated microspheres can be treated with a streptavidin, avidin or anti-biotin conjugated to a dye of the invention, as described above.

Example 47

Preparation of Nucleotide-Dye Conjugates

Nucleotides conjugated with the dyes of invention can be readily prepared by someone skilled in the art following the well known, published procedures, such as those described in M. Nimmakayalu et al., 2000, Biotechniques 28, 518-522; Muhlegger et al., 1990, Biol Chem Hoppe Seyler 371, 953-965; and Giaid et al., 1989, Histochemistry 93, 191-196, each incorporated herein by reference. Examples of particular conjugations are described, below.

To 2 mg of 5-(3-aminoallyl)-2'-deoxyuridine 5'-triphosphate (Sigma-Aldrich) in 100 µl water is added Compound 7, 13, 14, 19, 25 or 60 in 100 µL DMF and 5 µL triethylamine. After 3 hours, the solution is evaporated and the residue is purified by HPLC. The product fractions are lyophilized to give fluorescent nucleotide conjugate.

Alternatively, fluorescent dye-conjugates of deoxyuridine 5'-triphosphate are prepared from 5-(3-amino-1-propynyl)-2'-deoxyuridine 5'-triphosphate, or by treating a thiolated nucleotide or a thiophosphate nucleotide with a thiol-reactive dye of the invention (such as the maleimide Compound 9).

Alternatively, 2'-(or 3')-2-aminoethylaminocarbonyladenosine 5'-triphosphate is reacted with a slight excess of Compound 7, 13, 14, 19, 25 or 60, following precipitation with ethanol, the ribose-modified product is purified by preparative HPLC.

Example 48

Preparation of Oligonucleotide-Dye Conjugates

A 5'-amine-modified, 18-base M13 primer sequence (about 100 µg) is dissolved in 4 µl water. To this is added 250 µg of Compound 7, 13, 14, 19, 25 or 60 in 100 µl 0.1 M sodium borate, pH 8.5. After 16 hours, 10 µl of 5 M NaCl and 3 volumes of cold ethanol are added. The mixture is cooled to $-20°$ C., centrifuged, the supernatant is decanted, the pellet is rinsed with ethanol, and the pellet is then dissolved in 100 µL water. The labeled oligonucleotide is purified by HPLC. The desired peak is collected and evaporated to give the fluorescent oligonucleotide-dye conjugate.

Example 49

Cell Analysis by Flow Cytometry Using Dye-Antibody Conjugates

Analyte-specific antibodies conjugated to a dye compound of the present invention (i.e, labeled antibodies) are useful for the analysis of blood cells (for example, in whole blood samples) by flow cytometry. The labeled-antibodies are used to label (stain) cellular proteins, and the labeled cells are detected using a flow cytometer.

Samples (100 µL) of whole blood (preferably collected in EDTA) typically are stained with antibody-dye conjugate for 30-60 minutes in the dark at a dye-conjugate concentration of 1 µg or less per 0.1 ml of blood. Following staining, 2 mL of 1×FACS™ Lysing Solution (BD Bioscience, San Jose, Calif.) are added to the sample, the sample is mixed at medium speed on vortex mixer and then incubated at room temperature for 10 min. The sample is centrifuged at 2-500 g (preferably 2-300) for 5 minutes and the supernatant is decanted. The sample is washed (resuspended in 2 mL of 0.5% BSA/PBS wash buffer, mixed, and centrifuged) twice, re-suspended in either 0.5 mL of wash buffer or 150 µl of Fixation Stabilization Buffer, and held at 4° C. until flow cytometric analysis.

Analysis of the stained cells preferably is carried out using a BD LSR II flow cytometer (BD Biosciences, San Jose, Calif.) equipped with a blue (488 nm), a red (~633 nm), and a violet (405 nm) laser. The detection optics includes detection in a 525/50 nm fluorescence detection channel. Fluorescent biopolymers incorporating dye compounds such as Compound 7, 13, and 25 exhibit an excitation maximum closely matching the 405 nm emission of the violet laser, and the emission from the biopolymers is measured in the 525/50 nm detection channel. The flow cytometer is setup following the manufacturer's instructions. Flow cytometric analysis of the sample of stained cells is carried out according to the manufacturer's protocols, and the data is analyzed using standard techniques well known in the field to obtain the median fluorescence intensity for the cell population of interest.

It will be understood that the particular antibody conjugate used and the specific reaction components and particular reaction conditions used can have an effect on the results obtained. Routine experimentation should be carried out to determine preferred reaction components, such as buffers or lyse solutions, and reaction conditions, including staining times and temperatures. Such routine optimization of assay conditions is standard practice in the field of immunostaining-based assays.

Example 50

Dye-Conjugates of Anti-CD4, CD8 and CD45 Antibodies

Dye-conjugates were prepared using antibodies specific to CD4 and CD45 (clones SK3 and 2D1, respectively, from BD Biosciences, San Jose, Calif.), each conjugated, in separate preparations, to Compounds 7, 13, and 25, over a range of dye-to-protein ratios. The antibody-dye conjugates were prepared essentially as described in example 42, above. The antibody-conjugates of the CD4 and CD45 antibodies were used to analyze lymphocytes in whole blood samples, essentially as described in example 49, above.

The data indicated an optimal dye-to-protein ratio for each antibody-dye pair. For each antibody, the optimal dye-to-protein ratio for each of the three dyes occurred at similar ratios. Comparing the different antibodies conjugated to the same dyes, the optimal dye-to-protein ratios were significantly different, with optimal fluorescence observed at a higher ratio for CD4. In these experiments, no appreciable self-quenching was observed with the CD4 dye-conjugates having dye-to-protein ratios higher than the optimal ratio (over the tested range)—the fluorescence remained at the optimal level. In contrast, significant self-quenching was observed with CD45 dye-conjugates having a dye-to-protein ratio higher than the optimal ratio. Comparing the maximum fluorescence staining obtained using each dye compound, Compound 7 yielded better fluorescence staining than did Compound 13, which yielded better fluorescence staining than did Compound 25.

The results indicate that all three dye-conjugates are useful in preparing antigen-specific detection reagents for immunofluorescence assays analyzed by flow cytometry. In general, each the optimal dye-to-protein ratio is determined empirically (by routine optimization) for each specific antibody to be labeled.

Example 51

Dye-Conjugates of Anti-CD3, CD4, CD8 and CD45 Antibodies

Dye-conjugates were prepared using four different antibodies, CD3, CD4, CD8, and CD45 antibodies (clones SK7, SK3, SK1, and 2D1, respectively, from BD Biosciences, San Jose, Calif.), each conjugated, in separate preparations, to Compound 7 over a range of dye/protein ratios. The antibody-dye conjugates were prepared essentially as described in example 42, above. The dye-conjugates of the CD3, CD4, CD8, and CD45 antibodies were used to analyze lymphocyte cells in whole blood samples, essentially as described in example 49, above.

Figure 3:
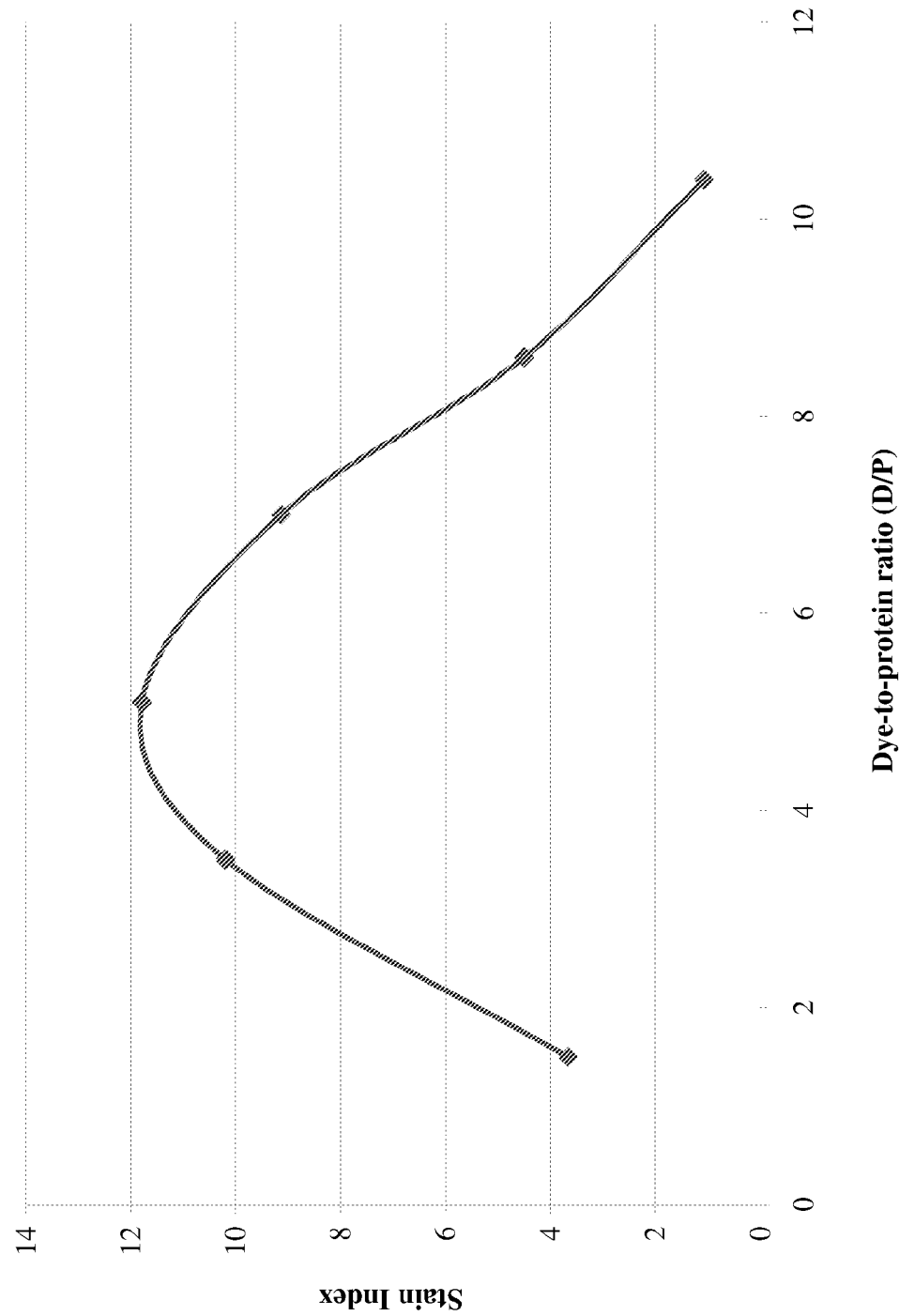
FIG. 3 shows a plot of the data obtained using dye-conjugates of CD3 antibodies conjugated to Compound 7 over a range of dye-to-protein ratios to label lymphocytes.
Figure 4:
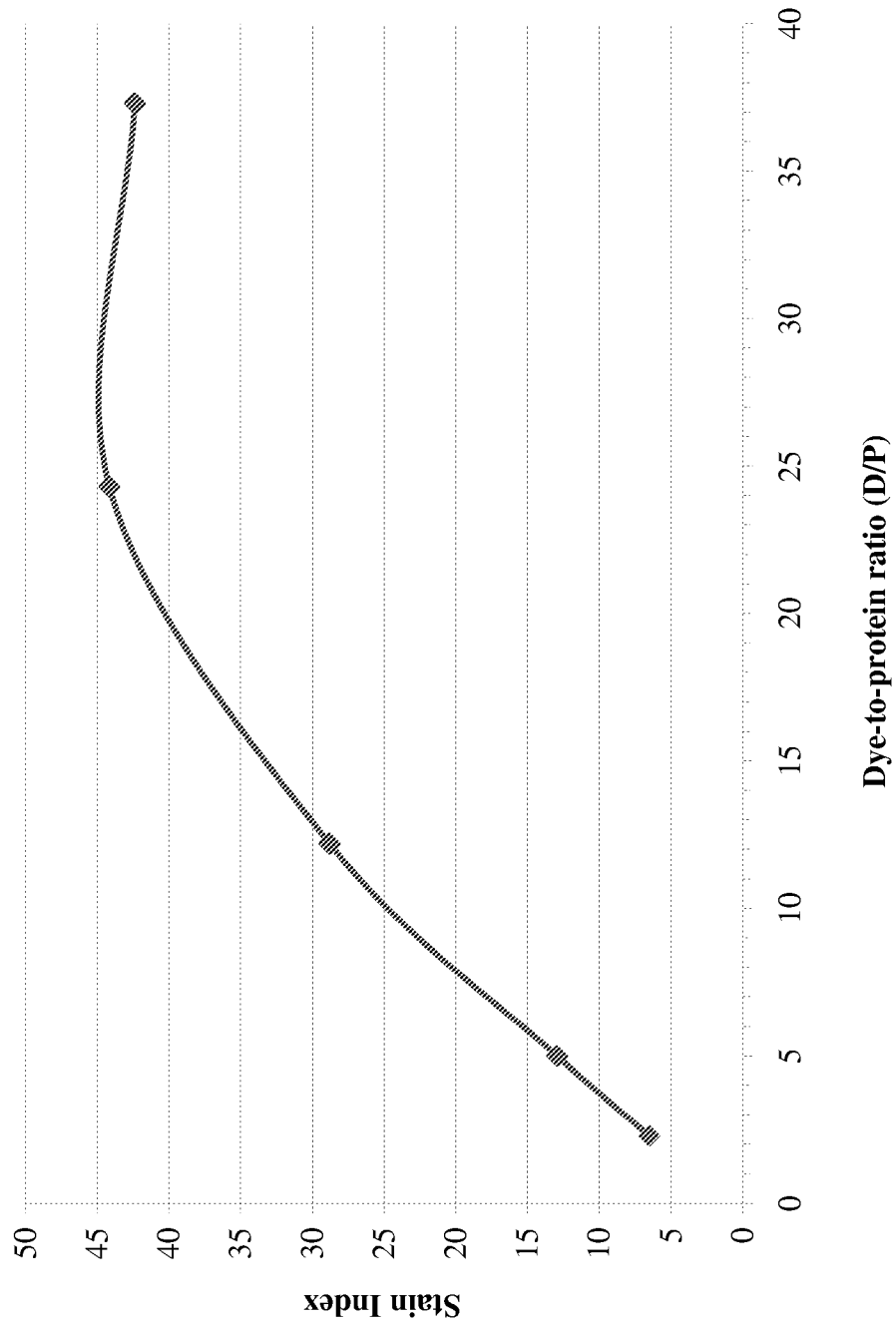
FIG. 4 shows a plot of the data obtained using dye-conjugates of CD4 antibodies conjugated to Compound 7 over a range of dye-to-protein ratios to label lymphocytes.
Figure 5:
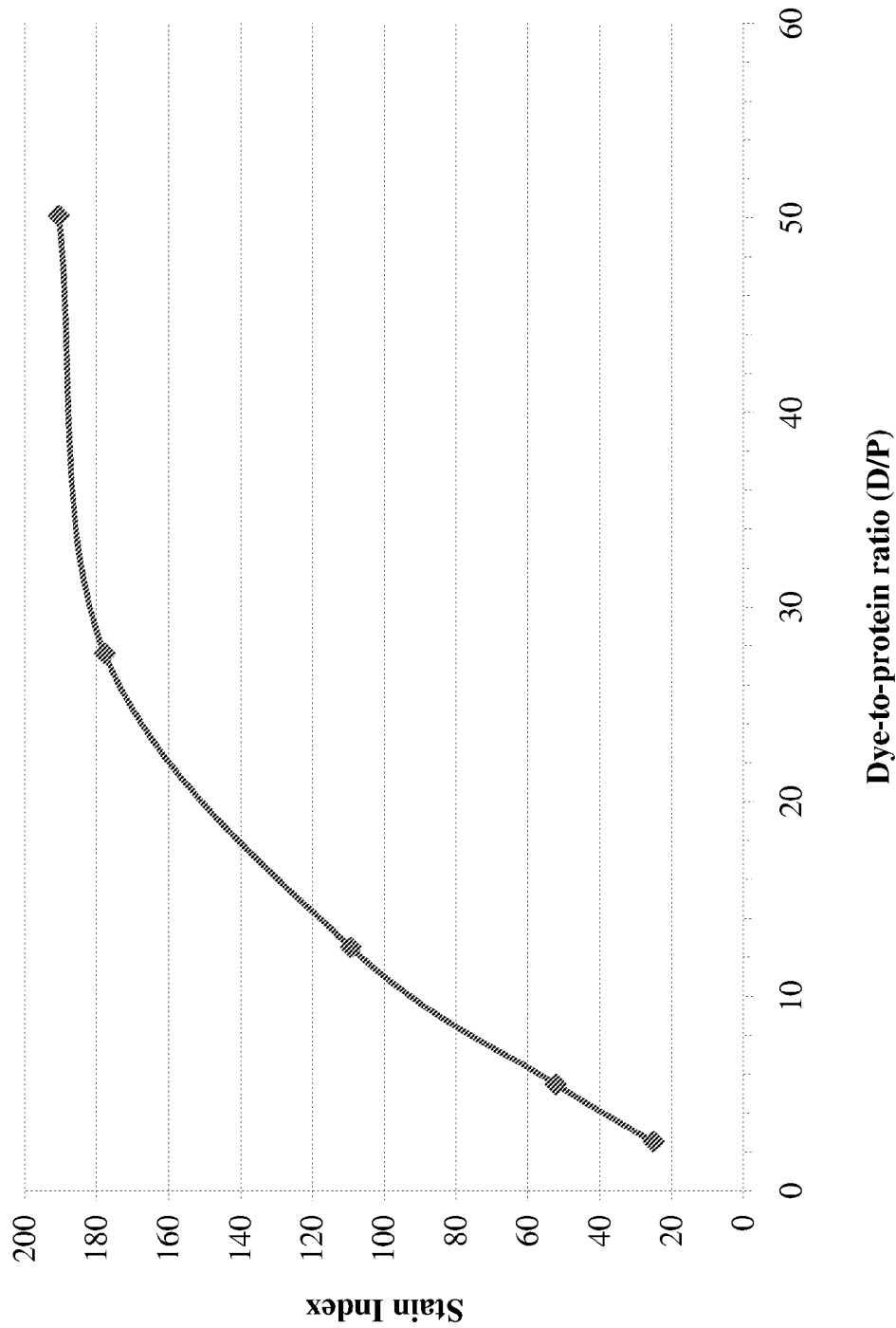
FIG. 5 shows a plot of the data obtained using dye-conjugates of CD8 antibodies conjugated to Compound 7 over a range of dye-to-protein ratios to label lymphocytes.
Figure 6:
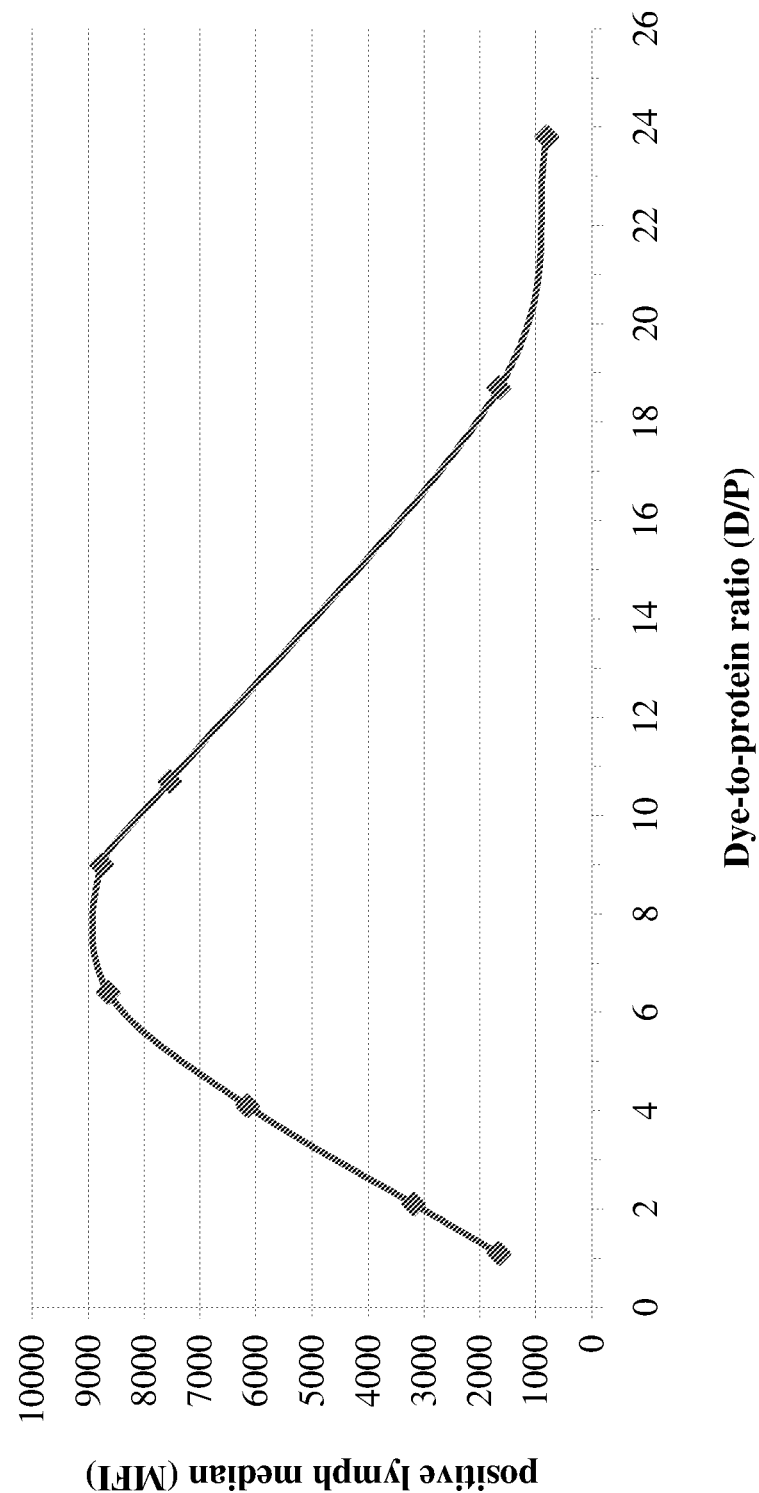
FIG. 6 shows a plot of the data obtained using dye-conjugates of CD45 antibodies conjugated to Compound 7 over a range of dye-to-protein ratios to label lymphocytes.

The results of the analyses are summarized in FIGS. 3-6, which show plots of the fluorescence intensity of the lymphocyte population labeled by the dye-conjugate, plotted against the dye-to-protein ratio for each dye-conjugate. In FIGS. 3-5, the fluorescence intensity is reported as a "stain index" that provides a measure of the fluorescence intensity of a stained cell population over the signal measured from an unstained, "negative" population (i.e., background), relative to the width of the distribution of fluorescence measured from the unstained population (see Maecker et al, 2004, Cytometry Part A 62A:169-173, incorporated herein by reference). The stain index is defined as:

$$\text{stain index} = (S-U)/(2*SD\_negative),$$

wherein S is the median fluorescence intensity (MFI) measured from the stained cell population, U the MFI of an unstained cell population, and SD_negative is the standard deviation of the fluorescence intensity of the unstained cell population. In FIG. 6, the fluorescence intensity is reported as the Median Fluorescent Intensity (MFI). Because CD45 antibody binds to all lymphocytes, there were no unstained lymphocyte populations to be used as a measure of background in these experiments, and the stain index could not be calculated.

The optimal dye-to-protein ratios for each of the dye-conjugated antibodies is provided in Table 4, below.

TABLE 4

| Optimal Dye-to-Protein Ratios | |
|---|---|
| Antibody Specificity | Optimal Dye-to-Protein Ratio |
| CD3 | 5 |
| CD4 | 25 |
| CD8 | 28 |
| CD45 | 9 |

FIG. 3 shows a plot of the data obtained using dye-conjugates of CD3 antibodies conjugated to Compound 7 over a range of dye-to-protein ratios. The maximum stain index obtained demonstrates that dye-conjugates of this CD3 antibody labeled with Compound 7 enables discrimination of the stained lymphocyte population over background fluorescence in a flow cytometric immunofluorescence assay. For this antibody and dye combination, self-quenching was observed at dye-to-protein ratios above the optimal.

FIG. 4 shows a plot of the data obtained using dye-conjugates of CD4 antibodies conjugated to Compound 7 over a range of dye-to-protein ratios. The maximum stain index obtained demonstrates that dye-conjugates of this CD4 antibody labeled with Compound 7 enables discrimination of the stained lymphocyte population over background fluorescence in a flow cytometric immunofluorescence assay. For this antibody and dye combination, little self-quenching was observed at dye-to-protein ratios above the optimal, providing a broad range of useable ratios.

FIG. 5 shows a plot of the data obtained using dye-conjugates of CD8 antibodies conjugated to Compound 7 over a range of dye-to-protein ratios. The maximum stain index obtained demonstrates that dye-conjugates of this CD8 antibody labeled with Compound 7 enables discrimination of the stained lymphocyte population over background fluorescence in a flow cytometric immunofluorescence assay. For this antibody and dye combination, little self-quenching was observed at dye-to-protein ratios above the optimal, providing a broad range of useable ratios.

FIG. 6 shows a plot of the data obtained using dye-conjugates of CD45 antibodies conjugated to Compound 7 over a range of dye-to-protein ratios. As the MFI depends on, for example, the photodetector gain the maximum MFI obtained does not directly indicate the utility of the dye-conjugate for distinguishing cell populations. However, the dye-conjugates of this CD45 antibody labeled with Compound 7 were observed to provide adequate labeling of lymphocyte populations for use in flow cytometric immunofluorescence assays. For this antibody and dye combination, self-quenching was observed at dye-to-protein ratios above the optimal, indicating that a narrower range of useable ratios.

What is claimed is:

1. A dye-conjugate having the formula:

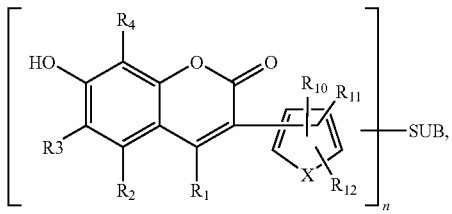

wherein
X is O or S;
$R_1$, $R_2$, $R_3$, $R_4$, $R_{10}$, $R_{11}$, and $R_{12}$ are independently H, halogen, alkyl, alkoxy, aryloxy, thiol, alkylthiol, arylthiol, azido, amino, hydroxy, boronic acid, WSG, or substituted alkyl or substituted alkoxy, wherein the substituted alkyl or substituted alkoxy is substituted one or more times by halogen, amino, hydroxy, carbonyl, boronic acid, or WSG;
WSG is a water-soluble group, wherein WSG is a sulfonate, a thiosulfonate, a phosphonate, a boronate, an ammonium, a pyridium, a quinolium or an acridinium;
n is an integer of 1-35;
SUB is a substrate, wherein SUB is a biopolymer;
at least one of $R_{10}$, $R_{11}$, and $R_{12}$ is covalently bound to the SUB through an optional linker L, wherein L is none, an alkyl, alkoxy, a thioalkyl, an amino acid, a sulfo amino acid, polyamine, a polyethyleneglycol, an aryl, or a heteroaryl; and
at least one of $R_{10}$, $R_{11}$, and $R_{12}$ is WSG.

2. The dye-conjugate of claim 1 wherein SUB is an antibody.

3. The dye-conjugate of claim 1 having the formula:

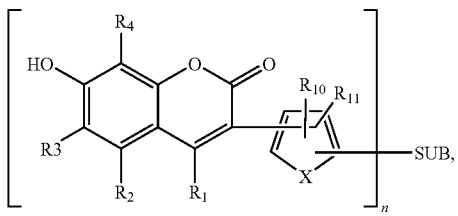

wherein
X is O or S;
$R_1$, $R_2$, $R_3$, $R_4$, $R_{10}$, and $R_{11}$ are independently H, halogen, alkyl, alkoxy, aryloxy, thiol, alkylthiol, arylthiol, azido, amino, hydroxy, boronic acid, WSG, or substituted alkyl or substituted alkoxy, wherein the substituted alkyl or substituted alkoxy is optionally substituted one or more times by halogen, amino, hydroxy, carbonyl, boronic acid, or WSG;
and at least one of $R_{10}$ and $R_{11}$ contains a sulfonate.

4. The dye-conjugate of claim 3 wherein SUB is an antibody.

5. The dye-conjugate of claim 1 having the formula:

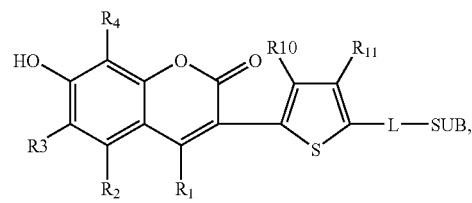

wherein
$R_1$, $R_2$, $R_3$, $R_4$, $R_{10}$, and $R_{11}$ are independently hydrogen, chloro, fluoro, or sulfonate; and
wherein at least one of $R_{10}$ and $R_{11}$ is a sulfonate.

6. The dye-conjugate of claim 5 wherein SUB is an antibody.

7. A kit comprising at least a dye-conjugate of claim 1.

8. The dye-conjugate of claim 1 wherein $R_3$ is chloro.

9. The dye-conjugate of claim 1, wherein the dye of the dye-conjugate is water-soluble.

10. The dye-conjugate of claim 1, wherein the dye-conjugate exhibits maximum fluorescence at physiological pH.

11. The dye-conjugate of claim 1, wherein the dye-conjugate exhibits an absorbance maxima at or near 405 nm.

12. The dye-conjugate of claim 1, wherein n is at least three.

13. The dye-conjugate of claim 1, wherein n is at least 6.

14. The dye-conjugate of claim 12, wherein the dye-conjugate exhibits no self-quenching.

15. The dye-conjugate of claim 1 wherein $R_1$, $R_2$, $R_3$, and $R_4$ are independently H, chloro or fluoro.

16. The dye-conjugate of claim 15 wherein $R_3$ and $R_4$ are independently chloro or fluoro.

17. The dye-conjugate of claim 3 wherein $R_1$, $R_2$, $R_3$, and $R_4$ are independently H, chloro or fluoro.

18. The dye-conjugate of claim 17 wherein $R_3$ and $R_4$ are independently chloro or fluoro.

19. The dye-conjugate of claim 5 wherein $R_1$, $R_2$, $R_3$, and $R_4$ are independently H, chloro or fluoro.

20. The dye-conjugate of claim 19 wherein $R_3$ and $R_4$ are independently chloro or fluoro.

21. The dye-conjugate of claim 5 wherein $R_{10}$ is sulfonate.

22. The dye-conjugate of claim 5 wherein $R_{11}$ is sulfonate.

* * * * *